United States Patent
Miller

(10) Patent No.: US 9,814,787 B2
(45) Date of Patent: *Nov. 14, 2017

(54) LUCIFERIN AMIDES

(71) Applicant: University of Massachusetts, Boston, MA (US)

(72) Inventor: Stephen C. Miller, Cambridge, MA (US)

(73) Assignee: University of Massachusetts, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/172,509

(22) Filed: Jun. 3, 2016

(65) Prior Publication Data

US 2016/0279268 A1    Sep. 29, 2016

Related U.S. Application Data

(62) Division of application No. 13/839,791, filed on Mar. 15, 2013, now Pat. No. 9,370,588.

(60) Provisional application No. 61/749,139, filed on Jan. 4, 2013.

(51) Int. Cl.
| | |
|---|---|
| A61B 5/00 | (2006.01) |
| A61B 8/00 | (2006.01) |
| A61B 10/00 | (2006.01) |
| A61K 49/00 | (2006.01) |
| C07D 277/66 | (2006.01) |
| C07D 513/04 | (2006.01) |
| G01N 21/76 | (2006.01) |
| C07D 417/04 | (2006.01) |
| C07D 513/06 | (2006.01) |

(52) U.S. Cl.
CPC ...... A61K 49/0021 (2013.01); A61K 49/0045 (2013.01); C07D 277/66 (2013.01); C07D 417/04 (2013.01); C07D 513/04 (2013.01); C07D 513/06 (2013.01); G01N 21/763 (2013.01); A61K 49/0017 (2013.01)

(58) Field of Classification Search
None
See application file for complete search history.

(56) References Cited

U.S. PATENT DOCUMENTS

| | | | |
|---|---|---|---|
| 5,098,828 A | 3/1992 | Geiger et al. | |
| 7,910,087 B2 | 3/2011 | Miller | |
| 8,216,550 B2 | 7/2012 | Miller | |
| 8,765,969 B2 * | 7/2014 | Cali ................ | C12Q 1/66 548/178 |
| 9,370,588 B2 * | 6/2016 | Miller ................ | A61K 49/0045 |
| 2008/0299593 A1 | 12/2008 | Cali et al. | |
| 2012/0276564 A1 | 11/2012 | Miller | |

OTHER PUBLICATIONS

Shinde et al. (Biochemistry 2006, 45, 11103-11112).*
Branchini et al., "Naphthyl- and Quinolylluciferin: Green and Red Light Emitting Firefly Luciferin Analogues," *Photochemistry and Photobiology*, 49(5): 689-695 (1989).
Conley et al., "A Selenium Analogue of Firefly d-Luciferin with Red-Shifted Bioluminescence Emission," *Angew. Chem. Int. Ed.*, 51: 1-5 (2012).
Lang et al., "Substrate Specificity and Stereoselectivity of Rat Brain Microsomal Anandamide Amidohydrolase," *J. Med. Chem.*, 42: 896-9002 (1999).
McCutcheon et al., "Expedient Synthesis of Electronically Modified Luciferins for Bioluminescence Imaging," *J. Am. Chem. Soc., Communication*, 4 pages, A-D (2012).
Reddy et al., "Robust light emission from cyclic alkylaminoluciferin substrates for firefly luciferase", *J. Am. Chem. Soc.*, 132(3(: 13586-13587 (2010).
Van de Bittner et al., "In vivo imaging of hydrogen peroxide production in a murine tumor model with a chemoselective bioluminescent reporter," *PNAS*, 107(50): 21316-21321 (2010).
Wehrman et al., "Luminescent imaging of β-galactosidase activity in living subjects using sequential reporter-enzyme luminescence," *Nature Methods*, 3(4): 295-301 (2006).
Woodroofe et al., "N-Alkylated 6'-Aminoluciferins Are Bioluminescent Substrates for Ultra-Glo and QuantiLum Luciferase: New Potential Scaffolds for Bioluminescent Assays," *Biochemistry*, 47: 10383-10393 (2008).
Woodroofe et al., "Novel Heterocyclic Analogs of Firefly Luciferin," *Biochemistry, Just Accepted Manuscript*, pp. 1-28 (2012).
Wyffels et al., "Synthesis, In Vitro and In Vivo Evaluation, and Radiolabeling of Aryl Anandamide Analogues as Candidate Radioligands for In Vivo Imaging of Fatty Acid Amide Hydrolase in the Brain," *J. Med. Chem.*, 52:4613-4622 (2009).

* cited by examiner

*Primary Examiner* — Michael G Hartley
*Assistant Examiner* — Melissa J Perreira
(74) *Attorney, Agent, or Firm* — Fish & Richardson P.C.

(57) ABSTRACT

This disclosure relates to luciferin amides of formula (I) shown below:

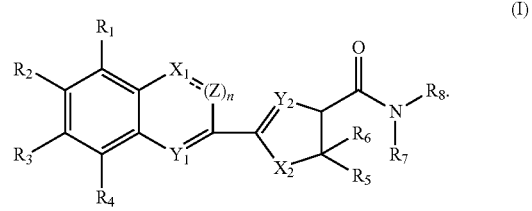

(I)

Each variable in formula (I) is defined in the specification. These compounds can be used to detect fatty acid amide hydrolase activities in vitro, in live cells, or in vivo.

25 Claims, 7 Drawing Sheets

FVB mice with AAV9-luciferase in the brain striatum were IP injected with 0.1 mL D-luciferin (100 mM), 0.1 mL CycLuc1 (5 mM), 0.06 mL CycLuc1 (0.5 mM), or 0.06 mL CycLuc1 amide (0.5 mM).

LUCIFERIN AMIDES

CROSS-REFERENCE TO RELATED APPLICATIONS

This application is a divisional of U.S. Utility application Ser. No. 13/839,791, filed on Mar. 15, 2013, which claims priority to U.S. Provisional Application No. 61/749,139, filed on Jan. 4, 2013. The contents of the prior applications are hereby incorporated by reference in their entirety.

TECHNICAL FIELD

This disclosure relates to luciferin amides, as well as methods of making and using these amides.

BACKGROUND

Fatty acid amide hydrolase (FAAH) is of great interest as a target for pharmaceuticals because fatty acid amides are important cellular messengers with critical roles in inflammation and analgesia. In particular, anandamide is an endogenous cannabinoid neurotransmitter involved in the regulation of pain, inflammation, and cognitive states. Because anandamide is primarily degraded by FAAH, this enzyme is being pursued as a biological target for treating the above-mentioned disorders. For example, it has been shown that FAAH inhibitors could reduce inflammatory pain.

However, current assays for FAAH activity are limited and typically require HPLC, radioactivity, or short-wavelength fluorescence for detection. None of these methods is suitable for rapid assays or imaging in live cells or organisms. Even in vitro, these assays are limited in terms of speed, sensitivity, and/or compound compatibility.

SUMMARY

This disclosure is based on the unexpected discovery that certain luciferin amides (e.g., amides derived from firefly luciferin and their analogs) can be used as selective bioluminescent sensors to detect FAAH activity in vitro, in live cells, and in vivo. In addition, it has been found unexpectedly that bioluminescent detection of FAAH activity with certain luciferin amides is much more sensitive than conventional coumarin-based FAAH sensors. Further, it has been found unexpectedly that certain luciferin amides allow the detection of bioluminescent signals from luciferase-expressing cells and animals at a much lower dosage than their corresponding luciferins.

In one aspect, this disclosure features luciferin amide compounds of formula (I):

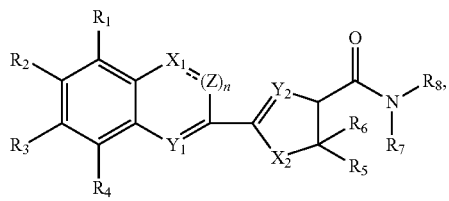

(I)

In this formula, n is 0 or 1; ═══ is deleted, a single bond, or a double bond; provided that, when n is 0, ═══ is deleted; each of $X_1$ and $X_2$, independently, is O, S, Se, N, $N(R_a)$, $C(R_a)$, or $C(R_aR_{a'})$, in which each of $R_a$ and $R_{a'}$, independently, is H or $C_1$-$C_{10}$ alkyl; provided that, when ═══ is a double bond, $X_1$ is N or $C(R_a)$; each of $Y_1$ and $Y_2$, independently, is N or $C(R_b)$, in which $R_b$ is H or $C_1$-$C_{10}$ alkyl; Z is $C(R_e)$ or $C(R_eR_{e'})$, in which each of $R_e$ and $R_{e'}$, independently, is H or $C_1$-$C_{10}$ alkyl; provided that, when ═══ is a single bond, Z is $C(R_eR_{e'})$ and that, when ═══ is a double bond, Z is $C(R_e)$; $R_2$ is H, $N(R_dR_{d'})$, or $OR_d$, in which each of $R_d$ and $R_{d'}$, independently, is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; each of $R_1$, $R_3$, $R_4$, $R_5$, and $R_6$, independently, is H, halo, CN, $OR_e$, $SR_e$, $NO_2$, $N(R_eR_{e'})$, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, in which each of $R_e$ and $R_{e'}$, independently, is H or $C_1$-$C_{10}$ alkyl; or $R_1$ and $R_2$, together with the carbon atoms to which they are attached, are a substituted or unsubstituted 5, 6, or 7-membered ring optionally fused with one or more substituted or unsubstituted 5, 6, or 7-membered rings; or $R_2$ and $R_3$, together with the carbon atoms to which they are attached, are a substituted or unsubstituted 5, 6, or 7-membered ring optionally fused with one or more substituted or unsubstituted 5, 6, or 7-membered rings; and each of $R_7$ and $R_8$, independently, is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl.

In another aspect, this disclosure features an imaging method. The method includes contacting a cell (e.g., in vitro or in an organism) containing a luciferase and a fatty acid amide hydrolase with one or more of the luciferin amide compounds described herein and detecting bioluminescent emission from the cell.

In another aspect, this disclosure features an imaging method that includes contacting a cell containing a fatty acid amide hydrolase with one or more of the luciferin amide compounds described herein; introducing a luciferase; and detecting bioluminescent emission.

Other features, objects, and advantages of the subject matter described in this disclosure will be apparent from the description, drawings, and claims.

DESCRIPTION OF DRAWINGS

Like reference symbols in the various drawings indicate like elements.

DETAILED DESCRIPTION

Figure 1:
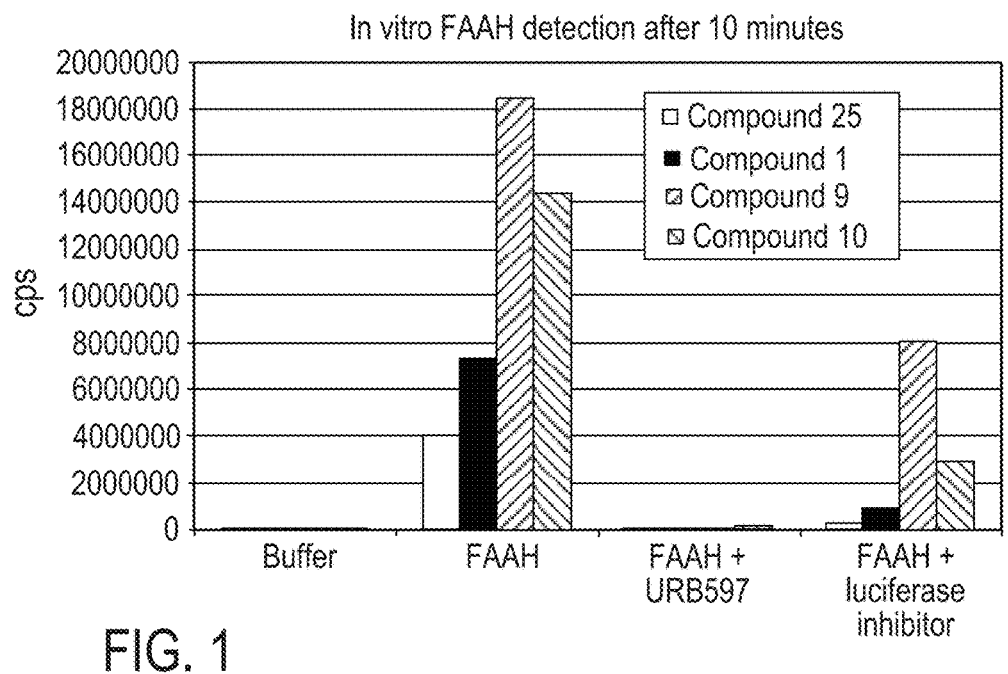
FIG. 1 is a graph illustrating in vitro detection of FAAH activity by using certain exemplary luciferin amides.

In general, this disclosure relates to luciferin amides, as well as methods of making and using these amides.

Luciferin Amides

In some embodiments, this disclosure relates to the luciferin amide compounds of formula (I):

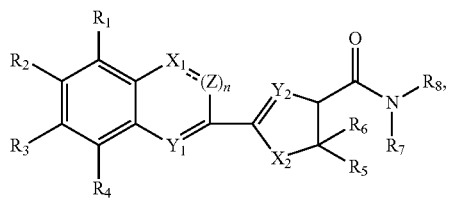

(I)

In this formula, n is 0 or 1; ≡≡≡ is deleted, a single bond, or a double bond; provided that, when n is 0, ≡≡≡ is deleted; each of $X_1$ and $X_2$, independently, is O, S, Se, N, $N(R_a)$, $C(R_a)$, or $C(R_a R_{a'})$, in which each of $R_a$ and $R_{a'}$, independently, is H or $C_1$-$C_{10}$ alkyl; provided that, when ≡≡≡ is a double bond, $X_1$ is N or $C(R_a)$; each of $Y_1$ and $Y_2$, independently, is N or $C(R_b)$, in which $R_b$ is H or $C_1$-$C_{10}$ alkyl; Z is $C(R_e)$ or $C(R_e R_{e'})$, in which each of $R_e$ and $R_{e'}$, independently, is H or $C_1$-$C_{10}$ alkyl; provided that, when ≡≡≡ is a single bond, Z is $C(R_e R_{e'})$ and that, when ≡≡≡ is a double bond, Z is $C(R_e)$; $R_2$ is H, $N(R_d R_{d'})$, or $OR_d$, in which each of $R_d$ and $R_{d'}$, independently, is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; each of $R_1$, $R_3$, $R_4$, $R_5$, and $R_6$, independently, is H, halo, CN, $OR_e$, $SR_e$, $NO_2$, $N(R_e R_{e'})$, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, in which each of $R_e$ and $R_{e'}$, independently, is H or $C_1$-$C_{10}$ alkyl; or $R_1$ and $R_2$, together with the carbon atoms to which they are attached, are a substituted or unsubstituted 5, 6, or 7-membered ring (e.g., containing one or more heteroatoms such as O, N or S) optionally fused with one or more substituted or unsubstituted 5, 6, or 7-membered rings (e.g., containing one or more heteroatoms such as O, N or S); or $R_2$ and $R_3$, together with the carbon atoms to which they are attached, are a substituted or unsubstituted 5, 6, or 7-membered ring (e.g., containing one or more heteroatoms such as O, N or S) optionally fused with one or more substituted or unsubstituted 5, 6, or 7-membered rings (e.g., containing one or more heteroatoms such as O, N or S); and each of $R_7$ and $R_8$, independently, is H, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl.

The term "alkyl" refers to a saturated, linear or branched hydrocarbon moiety, such as —$CH_3$ or —$CH(CH_3)_2$. The term "alkenyl" refers to a linear or branched hydrocarbon moiety that contains at least one double bond, such as —CH=CH—$CH_3$. The term "alkynyl" refers to a linear or branched hydrocarbon moiety that contains at least one triple bond, such as —C≡C—$CH_3$. The term "cycloalkyl" refers to a saturated, cyclic hydrocarbon moiety, such as cyclohexyl. The term "cycloalkenyl" refers to a non-aromatic, cyclic hydrocarbon moiety that contains at least one double bond, such as cyclohexenyl. The term "heterocycloalkyl" refers to a saturated, cyclic moiety having at least one ring heteroatom (e.g., N, O, or S), such as 4-tetrahydropyranyl. The term "heterocycloalkenyl" refers to a non-aromatic, cyclic moiety having at least one ring heteroatom (e.g., N, O, or S) and at least one ring double bond, such as pyranyl. The term "aryl" refers to a hydrocarbon moiety having one or more aromatic rings. Examples of aryl moieties include phenyl (Ph), phenylene, naphthyl, naphthylene, pyrenyl, anthryl, and phenanthryl. The term "heteroaryl" refers to a moiety having one or more aromatic rings that contain at least one heteroatom (e.g., N, O, or S). Examples of heteroaryl moieties include furyl, furylene, fluorenyl, pyrrolyl, thienyl, oxazolyl, imidazolyl, thiazolyl, pyridyl, pyrimidinyl, quinazolinyl, quinolyl, isoquinolyl and indolyl.

Alkyl, alkenyl, alkynyl, cycloalkyl, cycloalkenyl, heterocycloalkyl, heterocycloalkenyl, aryl, and heteroaryl mentioned herein include both substituted and unsubstituted moieties, unless specified otherwise. Possible substituents on cycloalkyl, cycloalkenyl, heterocycloalkyl, heterocycloalkenyl, aryl, and heteroaryl include, but are not limited to, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, $C_1$-$C_{10}$ alkoxy, aryl, aryloxy, heteroaryl, heteroaryloxy, amino, $C_1$-$C_{10}$ alkylamino, $C_1$-$C_{20}$ dialkylamino, arylamino, diarylamino, $C_1$-$C_{10}$ alkylsulfonamino, arylsulfonamino, $C_1$-$C_{10}$ alkylimino, arylimino, $C_1$-$C_{10}$ alkylsulfonimino, arylsulfonimino, hydroxyl, halo, thio, $C_1$-$C_{10}$ alkylthio, arylthio, $C_1$-$C_{10}$ alkylsulfonyl, arylsulfonyl, acylamino, aminoacyl, aminothioacyl, amidino, guanidine, ureido, cyano, nitro, nitroso, azido, acyl, thioacyl, acyloxy, carboxyl, and carboxylic ester. On the other hand, possible substituents on alkyl, alkenyl, or alkynyl include all of the above-recited substituents except $C_1$-$C_{10}$ alkyl. Cycloalkyl, cycloalkenyl, heterocycloalkyl, heterocycloalkenyl, aryl, and heteroaryl also include moieties in which two or more rings are fused together, unless otherwise specified. For example, the term "heterocycloalkyl" includes a moiety in which a heterocycloalkyl group is fused with another ring (e.g., a heterocycloalkenyl group).

In some embodiments, in formula (I), each of $R_7$ and $R_8$, independently, can be H, aryl (e.g., phenyl optionally substituted with OH, amino, $C_1$-$C_{10}$ alkyl, or $C_1$-$C_{10}$ alkoxy), $C_3$-$C_{20}$ cycloalkyl (e.g., cyclohexyl optionally substituted with OH, $C_1$-$C_{10}$ alkyl, $C_1$-$C_{10}$ alkoxy), $C_2$-$C_{10}$ alkenyl (e.g., allyl), $C_2$-$C_{10}$ alkynyl (e.g., propargyl), or $C_1$-$C_{10}$ alkyl optionally substituted with OH, halo (e.g., F, Cl, or Br), or aryl (e.g., phenyl optionally substituted with OH, $C_1$-$C_{10}$ alkyl, or $C_1$-$C_{10}$ alkoxy). For example, each of $R_7$ and $R_8$, independently, can be H, $CH_3$, $CH_2CH_3$, $CH_2CH_2CH_3$, $CH_2CH_2CH_2CH_3$, $CH_2CH(CH_3)_2$, $CH(CH_3)CH_2CH_3$, $CH_2C(CH_3)_3$, $CH_2CH_2CH_2CH_2CH_3$, $CH_2CH=CH_2$, $CH_2C≡CH$, $CH_2CF_3$, $CH_2CH_2OH$, $CH_2CH_2F$, $CH(CH_3)CH_2OH$, $C(CH_3)_2CH_2OH$, $CH_2CH(CH_3)OH$, $CH_2Ph$, $CH_2CH_2Ph$, Ph-OH, Ph-$CH_2OH$, $CH_2CH_2$-Ph-I, $CH_2$-Ph-I, or $CH_2CH_2$-Ph-$OCH_3$.

Referring to formula (I), a subset of the luciferin amides described above are those in which n is 0 and ≡≡≡ is deleted. In these compounds, each of $X_1$ and $X_2$ can be S and each $Y_1$ and $Y_2$ can be N. Such compounds can be of formula (II):

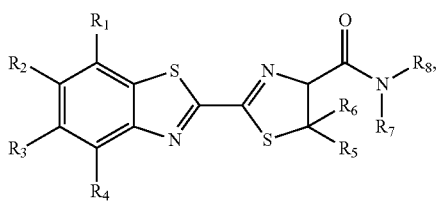

(II)

in which $R_1$-$R_8$ are defined above.

Referring to formula (II), a subset of the luciferin amides described above are those in which $R_2$ is $NR_dR_{d'}$, in which each of $R_d$ and $R_{d'}$, independently, is H or $C_1$-$C_{10}$ alkyl optionally substituted with OH (e.g., $CH_2CH_3$, $CH(CH_3)_2$, $(CH_2)_3$—OH, or $CH_2CH(CH_3)_2$). In these compounds, each of $R_1$, $R_3$, $R_4$, $R_5$, and $R_6$ can be H and each of $R_7$ and $R_8$, independently, can be H or $C_1$-$C_{10}$ alkyl optionally substituted with OH (e.g., $CH_3$ or $CH_2CH_2OH$). Examples of such luciferin amides include:

Compound 1

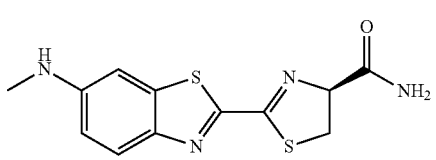

Compound 2

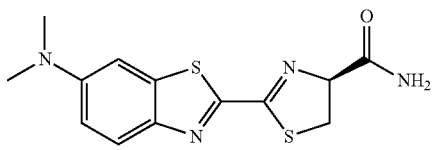

Compound 3

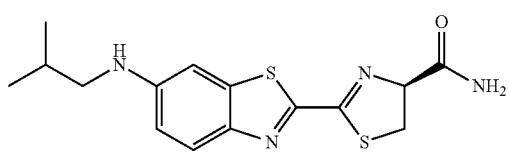

Compound 4

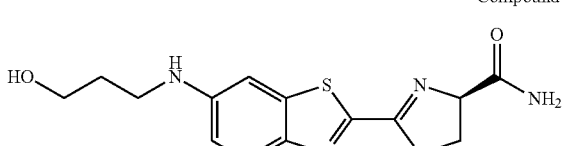

Compound 5

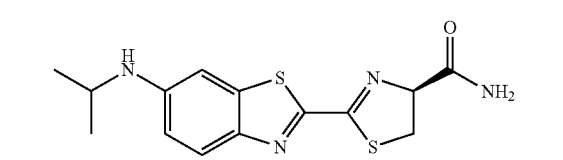

Compound 6

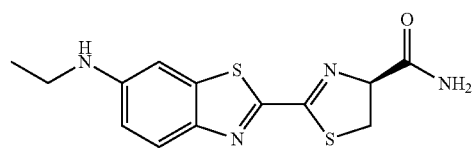

Compound 7

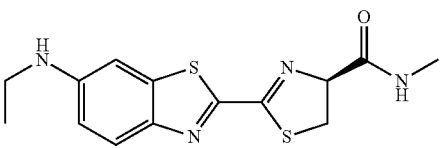

Compound 8

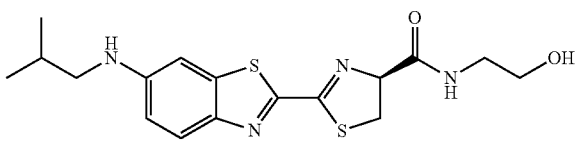

Compound 29

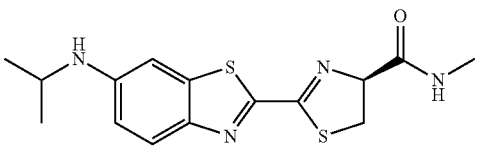

Compound 30

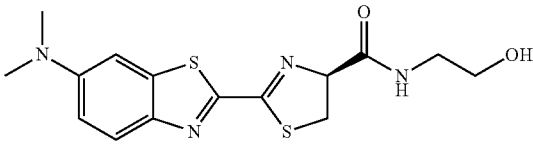

Referring to formula (II), another subset of the luciferin amides described above are those in which $R_2$ and $R_3$, together with the carbon atoms to which they are attached, are a 5 or 6-membered ring (e.g., containing one or more heteroatoms such as O, N or S), each of which is optionally substituted with $C_1$-$C_{10}$ alkyl (e.g., $CH_3$) or optionally fused with a 5 or 6-membered ring (e.g., containing one or more heteroatoms such as O, N or S). For example, $R_2$ and $R_3$, together with the carbon atoms to which they are attached, can be a 5-membered ring optionally substituted with $CH_3$, or a 6-membered ring optionally substituted with $CH_3$ and/or optionally fused with a 5-membered ring. In these compounds, each of $R_1$ and $R_4$, independently, can be H, OH, or $C_1$-$C_{10}$ alkyl; each of $R_5$ and $R_6$ can be H; and each of $R_7$ and $R_8$, independently, can be H or $C_1$-$C_{10}$ alkyl. Examples of such luciferin amides include:

Compound 9

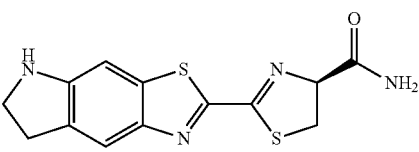

Compound 10

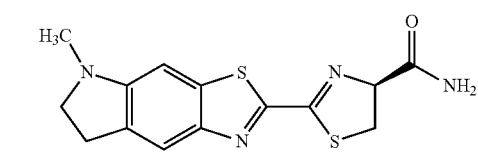

Compound 11
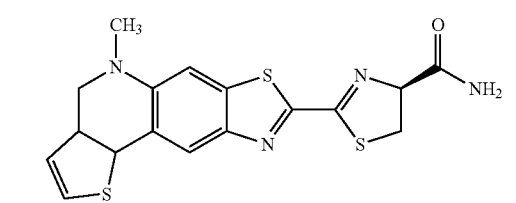

Compound 12
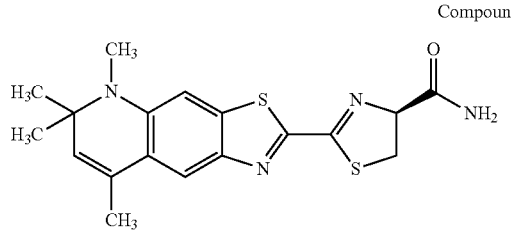

Compound 13
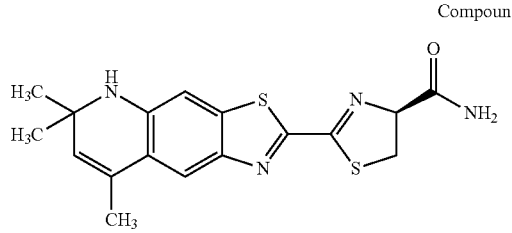

Compound 14
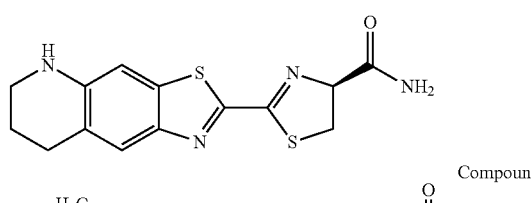

Compound 15
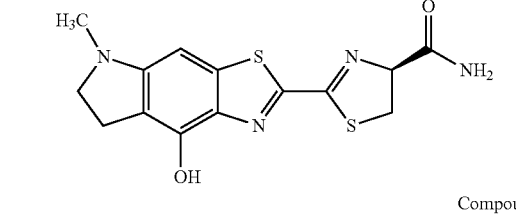

Compound 16
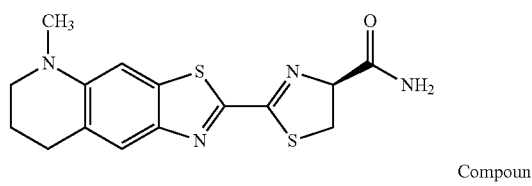

Compound 17
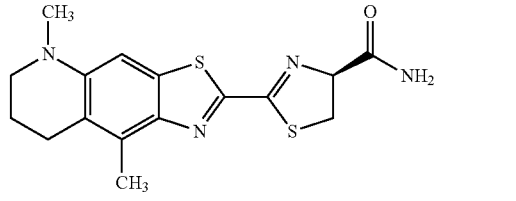

Compound 18
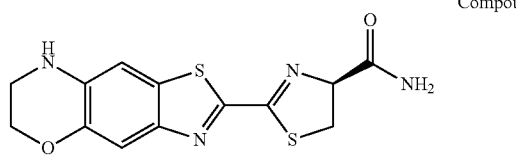

Compound 19
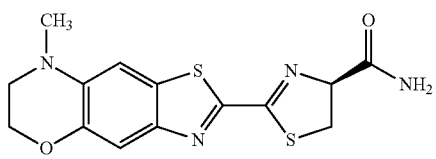

Compound 20
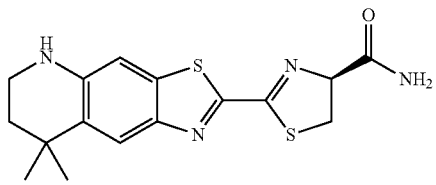

Compound 21
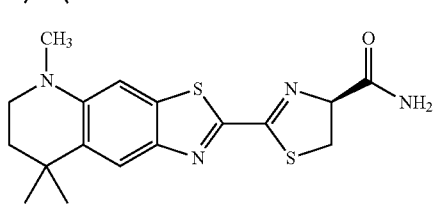

Compound 31
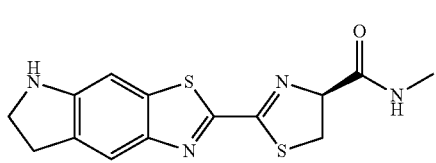

Compound 32
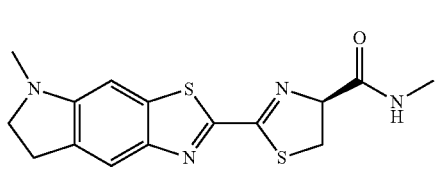

Referring to formula (II), another subset of the luciferin amides described above are those in which $R_1$ and $R_2$, together with the carbon atoms to which they are attached, are a 6-membered ring optionally substituted with $C_1$-$C_{10}$ alkyl (e.g., $CH_3$). In these compounds, each of $R_3$, $R_4$, $R_5$, $R_6$, $R_7$, and $R_8$ can be H. Examples of such luciferin amides include:

Compound 22
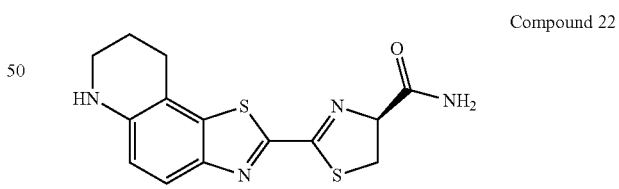

Compound 23
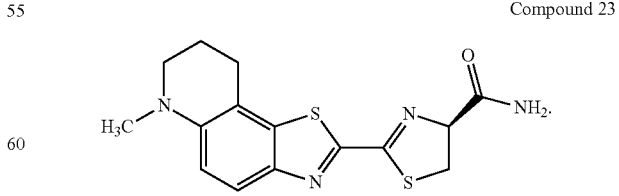

Referring to formula (II), another subset of the luciferin amides described above are those in which $R_1$ and $R_2$, together with the carbon atoms to which they are attached, are a 6-membered ring optionally substituted with $C_1$-$C_{10}$ alkyl and $R_2$ and $R_3$, together with the carbon atoms to which they are attached, are a 6-membered ring optionally substituted with $C_1$-$C_{10}$ alkyl. In these compounds, each of $R_4$, $R_5$, $R_6$, $R_7$, and $R_8$ can be H. An example of such a luciferin amide is:

Compound 24

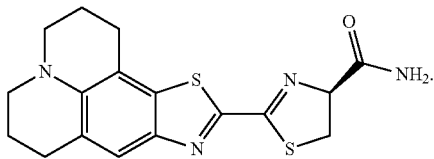

Referring to formula (II), another subset of the luciferin amides described above are those in which $R_2$ is $OR_d$, in which $R_d$ is H or $C_1$-$C_{10}$ alkyl optionally substituted with aryl (e.g., $CH_3$ or $CH_2Ph$). In these compounds, $R_2$ can be OH, $OCH_3$, or $OCH_2Ph$, and each of $R_1$, $R_3$, $R_4$, $R_5$, $R_6$, $R_7$, and $R_8$ can be H. Examples of such luciferin amides include:

Compound 25

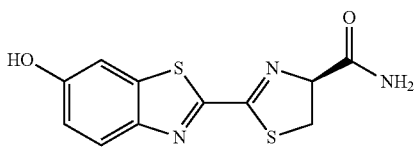

Compound 26

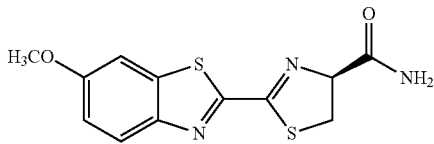

Compound 27

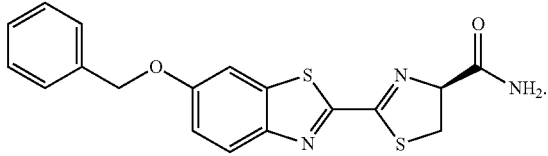

Referring to formula (II), another subset of the luciferin amides described above are those in which $R_2$ is H. An example of such a luciferin amide is Compound 28

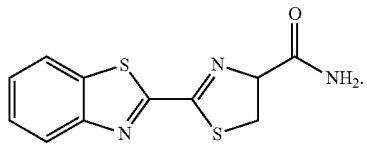

In some embodiments, when n in formula (I) is 0 and ≡ in formula (I) is deleted, a subset of the luciferin amides described above are those in which $X_1$ can be O, S, Se, $N(R_a)$, in which $R_a$ is H or $C_1$-$C_{10}$ alkyl (e.g., $CH_3$); $X_2$ can be S; $Y_1$ can be N or $C(R_b)$, in which $R_b$ is H or $C_1$-$C_{10}$ alkyl (e.g., $CH_3$); and $Y_2$ can be N. For example, when $X_1$ is O, $X_2$ can be S; $Y_1$ can be N or $C(R_b)$, in which $R_b$ is H or $C_1$-$C_{10}$ alkyl (e.g., $CH_3$); and $Y_2$ can be N. As another example, when $X_1$ is S, $X_2$ can be S or Se; $Y_1$ can be $C(R_b)$, in which $R_b$ is H or $C_1$-$C_{10}$ alkyl (e.g., $CH_3$); and $Y_2$ can be N. As another example, when $X_1$ is $N(R_a)$, in which $R_a$ is H or $C_1$-$C_{10}$ alkyl (e.g., $CH_3$); $X_2$ can be S; $Y_1$ can be N; and $Y_2$ can be N. In some of these compounds, $R_2$ can be $N(R_dR_{d'})$ or $OR_d$, in which each of $R_d$ and $R_{d'}$, independently, is H or $C_1$-$C_{10}$ alkyl; and each of $R_1$, $R_3$, $R_4$, $R_5$, $R_6$, $R_7$, and $R_8$, independently, can be H or $C_1$-$C_{10}$ alkyl. In some of these compounds, $R_3$ can be $N(R_eR_{e'})$ or $OR_e$, in which each of $R_e$ and $R_{e'}$, independently, is H or $C_1$-$C_{10}$ alkyl; and each of $R_1$, $R_2$, $R_4$, $R_5$, $R_6$, $R_7$, and $R_8$, independently, can be H or $C_1$-$C_{10}$ alkyl.

Referring to formula (I), another subset of the luciferin amides described above are those in which n is 1, ≡ is a double bond, $X_1$ is $C(R_a)$, and Z is $C(R_e)$, in which $R_a$ is H or $C_1$-$C_{10}$ alkyl and $R_e$ is H or $C_1$-$C_{10}$ alkyl. In these compounds, $X_2$ can be S; $Y_1$ can be N or $C(R_b)$, in which $R_b$ is H or $C_1$-$C_{10}$ alkyl (e.g., $CH_3$); $Y_2$ can be N. In some of these compounds, $R_2$ can be $N(R_dR_{d'})$ or $OR_d$, in which each of $R_d$ and $R_{d'}$, independently, is H or $C_1$-$C_{10}$ alkyl; and each of $R_1$, $R_3$, $R_4$, $R_5$, $R_6$, $R_7$, and $R_8$, independently, can be H or $C_1$-$C_{10}$ alkyl. In some of these compounds, $R_3$ can be $N(R_eR_{e'})$ or $OR_e$, in which each of $R_e$ and $R_{e'}$, independently, is H or $C_1$-$C_{10}$ alkyl; and each of $R_1$, $R_2$, $R_4$, $R_5$, $R_6$, $R_7$, and $R_8$, independently, can be H or $C_1$-$C_{10}$ alkyl.

The luciferin amides herein above include the compounds themselves, as well as their salts, prodrugs, and solvates, if applicable. A salt, for example, can be formed between an anion and a positively charged group (e.g., amino) on a luciferin amide. Suitable anions include chloride, bromide, iodide, sulfate, nitrate, phosphate, citrate, methanesulfonate, trifluoroacetate, acetate, malate, tosylate, tartrate, fumurate, glutamate, glucuronate, lactate, glutarate, and maleate. Likewise, a salt can also be formed between a cation and a negatively charged group (e.g., carboxylate) on a luciferin amide. Suitable cations include sodium ion, potassium ion, magnesium ion, calcium ion, and an ammonium cation such as tetramethylammonium ion. The luciferin amides also include those salts containing quaternary nitrogen atoms. Examples of prodrugs include esters, amides, carbamates, carbonates, and other pharmaceutically acceptable derivatives, which, upon administration to a subject, are capable of providing active luciferin amides. A solvate refers to a complex formed between an active luciferin amide and a pharmaceutically acceptable solvent. Examples of pharmaceutically acceptable solvents include water, ethanol, isopropanol, ethyl acetate, acetic acid, and ethanolamine.

Also within the scope of this invention is a pharmaceutical composition containing an effective amount of at least one luciferin amide described above and a pharmaceutical acceptable carrier.

The luciferin amides mentioned herein may contain a non-aromatic double bond and one or more asymmetric centers. Thus, they can occur as racemates and racemic mixtures, single enantiomers, individual diastereomers, diastereomeric mixtures, and cis- or trans-isomeric forms. All such isomeric forms are contemplated. In some embodiments, the luciferin amide compounds mentioned herein are in D-isomer forms (i.e., D-luciferin amides).

Methods of Preparing Luciferin Amides

The luciferin amides described herein can be prepared by methods well known in the art. Examples 1-22 below provide detailed descriptions of how Compounds 1-7, 9, 10, 14, 20-23, and 25-32 described above were actually prepared.

Scheme I shown below illustrates a typical synthetic route for synthesizing certain exemplary luciferin amides.

Scheme I

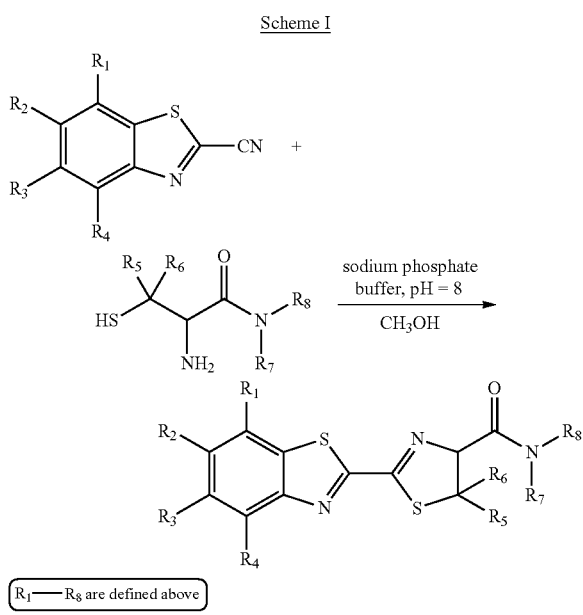

Specifically, as shown in Scheme I above, a luciferin amide described herein can be prepared by reacting a cyano-substituted benzothiazole with a substituted or unsubstituted 2-amino-3-mercaptopropanamide. The cyano-substituted benzothiazole can be prepared by methods known in the art, such as those described in commonly owned U.S. Pat. No. 7,910,087.

Other luciferin amides can be prepared using other suitable starting materials through the above synthetic routes and others known in the art. The methods described above may also include additional steps, either before or after the steps described specifically herein, to add or remove suitable protecting groups in order to ultimately allow synthesis of the luciferin amides. In addition, various synthetic steps may be performed in an alternate sequence or order to give the desired compounds. Synthetic chemistry transformations and protecting group methodologies (protection and deprotection) useful in synthesizing applicable luciferin amides are known in the art and include, for example, those described in R. Larock, *Comprehensive Organic Transformations*, VCH Publishers (1989); T. W. Greene and P. G. M. Wuts, *Protective Groups in Organic Synthesis*, 2$^{nd}$ Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

Methods of Using Luciferin Amides

In general, the luciferin amides described herein can be used in an imaging method for detecting FAAH activity. The method can include (1) contacting a cell containing a luciferase and a FAAH with one or more of the luciferin amides described herein, and (2) detecting bioluminescent emission from the cell.

The term "luciferase" as used herein refers to an enzyme that emits light (e.g., near-infrared or visible light) upon contact with its substrate (i.e., a luciferin). In some embodiments, the luciferase described herein can be a wild-type luciferase. Examples of wild-type luciferases include beetle luciferases, such as firefly, click beetle, and railroad worm luciferases.

In some embodiments, the luciferase described herein can be a mutant luciferase. For example, the binding pocket of the luciferase can be enlarged by mutation to accommodate a luciferin. In some embodiments, various amino acids in a luciferase can be altered, e.g., using standard site-directed mutagenesis methods, to amino acids with smaller side chains, thereby enlarging the binding pocket. For example, for substrate accommodation, amino acid residues corresponding to Arginine 218, Isoleucine 286, Serine 284, Serine 314, Alanine 313, Threonine 343 and/or Serine 347 of firefly luciferase can be altered. An example is a mutant luciferase that has a mutation at Serine 347 to alanine. As another example, for accessibility to solvent (e.g., fluorophore tethering), amino acid residues corresponding to Glutamate 311, Arginine 337 and/or Asparagine 229 of firefly luciferase can be altered. In general, conservative substitutions are desirable. Other mutant luciferases have been described in, e.g., Branchini et al., *Anal Biochem*, 2005, 345(1):140, Branchini et al., *Biochem.* 42 (2003) 10429-36, and commonly-owned co-pending PCT application WO2012/109470.

In general, the imaging method can be used in any cells or tissues that express a FAAH. In some embodiments, the FAAH is endogenously expressed in the cells or tissues to be detected. Examples of such cells or tissues include those from brain, liver, pancreas, testicle, kidney, white adipose tissue, and Chinese Hamster Ovary (CHO) cells. In other embodiments, the FAAH can be introduced into tissues or cells that have low or no endogenous FAAH expression (such as heart cells or brown adipose tissue). In such embodiments, the imaging method described above can further include introducing an exogenous gene into the cell to express a FAAH in the cell before contacting the cell with a luciferin amide.

In some embodiments, the luciferase can be expressed in a cell to be detected by introducing an exogenous gene into the cell before contacting the cell with a luciferin amide. In such embodiments, the imaging method described above can further include introducing an exogenous gene into the cell to express a luciferase in the cell before contacting the cell with a luciferin amide. In other embodiments, a cell expressing FAAH but without expressing a luciferase can first be contacted by a luciferin amide so that at least a portion of the luciferin amide is converted to a luciferin in the cell. A luciferase can subsequently be introduced (e.g., by lysing the cell and incubating with a recombinant luciferase protein) into the mixture thus formed. The FAAH activity can then be measured by detecting the bioluminescence emission generated from the mixture.

Without wishing to be bound by theory, it is believed that a luciferin amide described herein can be used to detect FAAH activity as follows: When a luciferin amide is introduced into a cell containing a luciferase (e.g., expressed in a cell by introducing an exogenous gene into the cell) and a FAAH, the luciferin amide is first converted to a corresponding luciferin by the FAAH (i.e., by converting the amide group to a carboxylic acid group under the FAAH's enzymatic action). The luciferin thus formed is a substrate of the luciferase in the cell and can emit light upon contact with the luciferase. Without wishing to be bound by theory, it is believed that the luciferin amides described herein themselves are not substrates to a luciferase and therefore would not substantially emit light upon contact with the luciferase in the absence of a FAAH. In other words, it is believed that the luciferin amides described herein would not substantially emit light when it is in contact with a cell containing a luciferase without a FAAH. As such, the luciferase amides described herein can be used to detect FAAH activity in cells either in vitro or in vivo.

In some embodiments, the luciferin amides described herein can unexpectedly exhibit a significantly higher sensitivity in detecting FAAH activity than conventional coumarin-based FAAH sensors. For example, the luciferin amides can be at least 100 times (e.g., at least 200 times, at least 300 times, at least 400 times, or at least 500 times) as sensitive as a conventional coumarin-based FAAH sensor. In addition, the luciferin amides can unexpectedly exhibit a significantly greater ability to elicit light emission from luciferase-expressing cells and tissues than their corresponding luciferins, particularly at low concentrations. For example, upon contacting cells in the brains of live mice expressing luciferase and FAAH, luciferin amides described herein can emit bioluminescence at an intensity similar to that obtained by contacting the corresponding luciferin with a luciferase but at a significantly lower dose.

In some embodiments, the production of a luciferin substrate from certain luciferin amides described herein (e.g., a prodrug of a luciferin amide) can require a second environmental condition or enzyme in addition to FAAH in order to be capable of supporting light emission from a luciferase. Examples of such enzymes include cytochrome P450 enzymes. For example, when a luciferin amide A whose corresponding luciferin A' itself does not elicit bioluminescence is used, luciferin amide A may be converted by a suitable enzyme (e.g., a cytochrome P450 enzyme) to a luciferin amide B whose corresponding luciferin B' elicits bioluminescence. Such a luciferin amide A can be used to detect activity of the enzyme that catalyzes the above-mentioned conversion. Similarly, such a luciferin amide A can also be used to detect activity of an enzyme that catalyzes the conversion of luciferin A' to luciferin B' in a cell.

For example, without wishing to be bound by theory, it is believed that Compound 26 can be used to detect activities of a cytochrome P450 enzyme as follows: When Compound 26 is introduced into a cell expressing a cytochrome P450 enzyme capable of catalyzing a demethylation reaction, a luciferase, and a FAAH, the methoxy group at the 6' position on the benzothiazole ring can be converted to a hydroxyl group by a cytochrome P450 enzyme and the amide group on the dihydrothiazole ring can be converted to a carboxylic acid group by the FAAH to form a luciferin (i.e., D-luciferin). The luciferin thus formed is a substrate of the luciferase in the cell and can emit light upon contact with the luciferase. Without wishing to be bound by theory, it is believed that Compound 26 would not substantially emit light when it is in contact with a cell expressing a luciferase and a FAAH in the absence of the above-mentioned cytochrome P450 enzyme as a luciferin having a methoxy group at the 6' position on the benzothiazole ring would not substantially emit light in the presence of a luciferase. As such, Compound 26 can be used to detect the activity of the above-mentioned cytochrome P450 enzyme in cells that also express FAAH. In some embodiments, Compound 27 can be used to detect activities of a cytochrome P450 enzyme capable of catalyzing a debenzylation reaction in cells in a manner similar to that described above with respect to Compound 26.

As another example, without wishing to be bound by theory, it is believed that Compound 28 can be used to detect activities of a cytochrome P450 enzyme as follows: When Compound 28 is introduced into a cell expressing a cytochrome P450 enzyme capable of catalyzing an oxidation reaction, a luciferase, and a FAAH, the 6' position on the benzothiazole ring can be oxidized to form a hydroxyl group by a cytochrome P450 enzyme and the amide group on the dihydrothiazole ring can be converted to a carboxylic acid group by the FAAH to form a luciferin (i.e., D-luciferin). The luciferin thus formed is a substrate of the luciferase in the cell and can emit light upon contact with the luciferase. Without wishing to be bound by theory, it is believed that Compound 28 would not substantially emit light when it is in contact with a cell expressing a luciferase and a FAAH in the absence of the above-mentioned cytochrome P450 enzyme as a luciferin having a proton at the 6' position on the benzothiazole ring would not substantially emit light in the presence of a luciferase. As such, Compound 28 can be used to detect the activity of the above-mentioned cytochrome P450 enzyme in cells that also express FAAH.

Without wishing to be bound by theory, it is believed that the imaging methods described herein are highly selective, as the luciferin amides are converted to their corresponding luciferins exclusively by FAAH. This is evidenced by the facts that the luciferin amides are not converted to their corresponding luciferins in the presence of FAAH inhibitors or in the presence of an enzyme other than FAAH alone. In some embodiments, 6'-alkylamino luciferin amides can be less prone to inhibition by luciferase inhibitors than D-luciferin or D-luciferin amide. In such embodiments, these luciferin amides can be preferentially used in high-throughput screening assays (e.g., to identify FAAH inhibitors) because "false positives" (i.e., inhibition of luciferase rather than inhibition of FAAH) are less likely to occur.

The imaging methods described herein can be used in vitro to detect FAAH activity in cultured cells or to screen for FAAH inhibitors (e.g., in a high-throughput screening process). Alternatively, the imaging methods described herein can be used in vivo to detect FAAH activity in live cells in a subject, such as, a human or a non-human animal. Examples of non-human animals include experimental animals, such as rodents (e.g., rats or mice). Transgenic mice expressing luciferase ubiquitously or driven by tissue-specific promoters can be purchased from commercial suppliers or created using standard Cre-lox technology. Luciferase-expressing cells can be introduced into rodents for imaging (e.g., tumor progression). Viral delivery vehicles such as adeno-associated viruses can be used to introduce luciferase into mouse tissues.

In some embodiments, the imaging methods described herein can be used in in vitro or in vivo assays to detect expression of luciferase in cells. Examples of such assays have been described in, e.g., commonly owned U.S. Pat. No. 7,910,087.

The methods described herein can be practiced with any suitable imaging system (e.g., an in vivo imaging system) that can detect bioluminescence (e.g., near infrared bioluminescence) by using a suitable detector (e.g., a sensitive CCD camera). Examples of such imaging systems have been described, e.g., in Doyle et al., *Cellular Microbiology* (2004) 6(4):303-317. Other suitable imaging systems are available from Perkin Elmer (e.g., Xenogen IVIS), Hamamatsu, Roper, and Kodak.

The contents of all publications cited herein (e.g., patents, patent application publications, and articles) are hereby incorporated by reference in their entirety.

The following examples are illustrative and not intended to be limiting.

EXAMPLE 1

Preparation of Compound 1: (S)-4,5-dihydro-2-(6-(methylamino)benzo[d]-thiazol-2-yl)thiazole-4-carboxamide

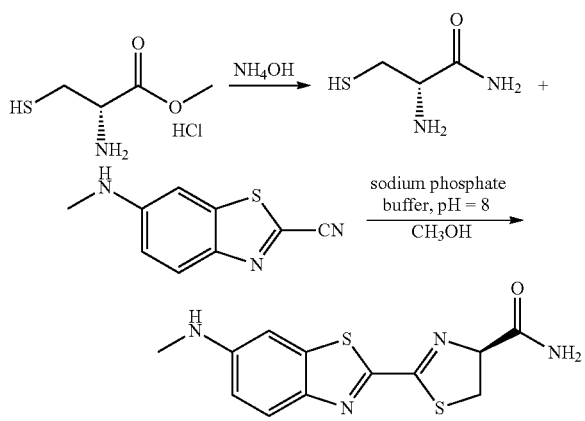

D-Cysteine methyl ester hydrochloride (500 mg, 2.912 mmol) was dissolved in aqueous ammonium hydroxide solution (3 mL). After the mixture was stirred at room temperature overnight, the solvent was partially evaporated under reduced pressure. The resulting precipitate was filtered and washed with ethyl acetate/hexane (1:1, 10 ml) to afford the desired product (S)-2-amino-3-mercaptopropanamide as a white solid (300 mg, 86%). $^1$H NMR (400 MHz, DMSO-$d_6$): δ 7.91 (br s, 1H), 7.49 (br s, 1H), 6.54 (brs, 3H), 3.79 (t, 1H, J=5.2 Hz), 2.90 (d, 2H, J=5.2 Hz). $^{13}$C NMR: 172.9, 55.0, 26.4.

(S)-2-amino-3-mercaptopropanamide obtained above (7 mg, 0.0634 mmol) was dissolved in 50 mM aqueous sodium phosphate buffer (pH 8, 2 mL). After the solution thus formed was degassed using argon, it was added to 6-(methylamino)benzo[d]-thiazole-2-carbonitrile (10 mg, 0.052 mmol) in 2 ml of degassed methanol. The resultant solution was stirred at room temperature for 2 hours, diluted with sodium phosphate buffer and extracted with ethyl acetate (2×30 mL). The combined organic layers were washed with water (3×30 mL), dried ($Na_2SO_4$), filtered, and concentrated to afford Compound 1 as a yellow solid (11 mg, 71%). $^1$H NMR (400 MHz, CDCl$_3$): δ 7.88 (d, 1H, J=8.8 Hz), 6.93 (d, 1H, J=2.0 Hz), 6.80 (dd, 1H, J=8.8, 2.4 Hz), 6.70 (br s, 1H), 5.66 (br s, 1H), 5.26 (t, 1H, J=10 Hz), 3.77 (d, 2H, J=9.6 Hz), 2.92 (s, 3H). $^{13}$C NMR (100 MHz, CDCl$_3$): δ 173.2, 166.9, 154.6, 149.2, 146.0, 139.0, 125.38, 115.79, 100.6, 79.0, 35.26, 30.8. HRMS (ESI$^+$) Calcd for $C_{12}H_{13}N_4OS_2$: 293.0531, Found: 293.0531.

EXAMPLE 2

Preparation of Compound 2: (S)-2-(6-(dimethylamino)benzo[d]thiazol-2-yl)-4,5-dihydrothiazole-4-carboxamide Compound 2 was prepared as an orange red solid (12 mg, 77%) in a manner similar to that described in Example 1 using suitable starting materials.

$^1$H NMR (400 MHz, CDCl$_3$): δ 7.94 (d, 1H, J=9.2 Hz), 7.02 (d, 1H, J=2.8 Hz), 6.97 (dd, 1H, J=9.2, 2.8 Hz), 6.71 (brs, 1H), 5.80 (brs, 1H), 5.26 (t, 1H, J=10.8 Hz), 3.77 (d, 2H, J=9.6 Hz), 3.07 (s, 6H). $^{13}$C NMR (100 MHz, CDCl$_3$): δ 173.4, 166.9, 154.6, 150.1, 145.2, 138.9, 125.1, 114.1, 101.9, 79.0, 40.9, 35.2. HRMS (ESI$^+$) Calcd for $C_{13}H_{15}N_4OS_2$: 307.0687, Found: 307.0672.

EXAMPLE 3

Preparation of Compound 3: (S)-4,5-dihydro-2-(6-(isobutylamino)benzo[d]-thiazol-2-yl)thiazole-4-carboxamide Compound 3 was prepared as a yellow solid (13 mg, 88%) in a manner similar to that described in Example 1 using suitable starting materials.

$^1$H NMR (400 MHz, CDCl$_3$): δ 7.87 (d, 1H, J=8.0 Hz), 6.92 (d, 1H, J=2.4 Hz), 6.79 (dd, 1H, J=2.4, 9.2 Hz), 6.70 (brs, 1H), 5.71 (brs, 1H), 5.26 (t, 1H, J=9.6 Hz), 4.15 (brs, 1H), 3.76 (d, 2H, J=9.6 Hz), 3.0 (d, 2H, J=7.2 Hz), 1.93 (m, 1H), 1.01 (d, 6H, J=6.8 Hz). $^{13}$C-NMR (100 MHz, CDCl$_3$): 173.3, 166.8, 154.5, 148.5, 145.8, 139.1, 125.4, 115.9, 100.9, 79.0, 59.1, 35.2, 28.2, 20.7. HRMS (ESI$^+$) Calcd for $C_{15}H_{19}N_4OS_2$: 335.1000, Found: 335.0965.

EXAMPLE 4

Preparation of Compound 4: (S)-2-(6-(3-hydroxypropylamino)benzo[d]-thiazol-2-yl)-4,5-dihydrothiazole-4-carboxamide Compound 4 was prepared as an orange red solid (12 mg, 69%) in a manner similar to that described in Example 1 using suitable starting materials.

$^1$H NMR (400 MHz, CDCl$_3$): δ 7.88 (d, 1H, J=9.2 Hz), 6.97 (d, 1H, J=2.0 Hz), 6.81 (dd, 1H, J=2.4, 8.8 Hz), 6.70 (br s, 1H), 5.63 (br s, 1H), 5.26 (1H, J=10 Hz), 3.85 (t, 2H, J=6.0 Hz), 3.77 (d, 2H, J=6.0 Hz), 3.35 (t, 2H, J=6.8 Hz), 1.94 (m, 2H). $^{13}$C NMR (100 MHz, CDCl$_3$): δ 173.3, 166.9, 155.1, 148.4, 146.0, 139.5, 125.4, 116.0, 101.1, 79.0, 61.6, 42.0, 35.2, 31.7. HRMS (ESI$^+$) Calcd for $C_{14}H_{17}N_4O_2S_2$: 337.0793, Found: 337.0793.

EXAMPLE 5

Preparation of Compound 5: (S)-4,5-dihydro-2-(6-(isopropylamino)-benzo[d]thiazol-2-yl)thiazole-4-carboxamide Compound 5 was prepared as a yellow solid (12 mg, 80%) in a manner similar to that described in Example 1 using suitable starting materials.

$^1$H NMR (400 MHz, CDCl$_3$): δ 7.86 (d, 1H, J=8.0 Hz), 6.92 (d, 1H, J=2.4 Hz), 6.75 (dd, 1H, J=2.4, 9.2 Hz), 6.71 (brs, 1H), 5.83 (brs, 1H), 5.26 (t, 1H, J=9.6 Hz), 3.76 (d, 2H, J=9.6 Hz), 3.69 (m, 1H), 1.26 (d, 6H, J=6.4 Hz). $^{13}$C-NMR (100 MHz, CDCl$_3$): 173.4, 166.8, 154.4, 147.4, 145.7, 139.1, 125.5, 116.1, 101.3, 79.0, 44.6, 35.2, 23.0. HRMS (ESI$^+$) Calcd for $C_{14}H_{17}N_4OS_2$: 321.0844, Found: 321.0837.

EXAMPLE 6

Preparation of Compound 6: (S)-2-(6-(ethylamino)benzo[d]thiazol-2-yl)-4,5-dihydrothiazole-4-carboxamide Compound 6 was prepared as a red solid (13 mg, 85%) in a manner similar to that described in Example 1 using suitable starting materials.

$^1$H NMR (400 MHz, CDCl$_3$): δ 7.87 (d, 1H, J=9.2 Hz), 6.93 (d, 1H, J=2.4 Hz), 6.79 (dd, 1H, J=9.2, 2.4 Hz), 6.70 (br s, 1H), 5.76 (br s, 1H), 5.26 (t, 1H, J=9.6 Hz), 3.76 (d, 2H, J=9.6 Hz), 3.23 (q, 2H, J=7.2 Hz) 1.31 (t, 3H, J=7.2 Hz). $^{13}$C NMR (100 MHz, CDCl$_3$): δ 173.4, 166.8, 154.6, 148.3, 145.9, 139.0, 125.4, 115.9, 100.9, 79.0, 38.6, 35.2, 14.8. HRMS (ESI$^+$) Calcd for C$_{13}$H$_{15}$N$_4$OS$_2$: 307.0687, Found: 307.0626.

EXAMPLE 7

Preparation of Compound 7: (S)-2-(6-(ethylamino)benzo[d]thiazol-2-yl)-4,5-dihydro-N-methylthiazole-4-carboxamide

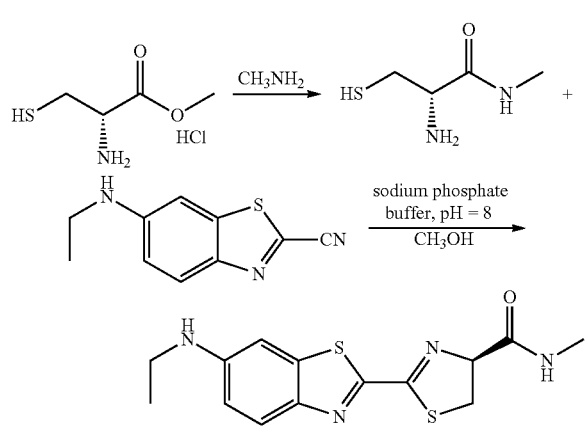

D-Cysteine methyl ester hydrochloride (500 mg, 2.912 mmol) was dissolved in 40% aqueous methylamine solution (3 mL). After the mixture was stirred at room temperature overnight, the solvent was partially evaporated under reduced pressure. The resultant precipitate was filtered and washed with ethyl acetate/hexane (1:1, 10 mL) to afford the desired product (S)-2-amino-3-mercapto-N-methylpropanamide as a white solid (300 mg, 76%). $^1$H NMR (400 MHz, D$_2$O): δ 3.90 (t, 1H, J=6.0 Hz), 2.94-2.73 (m, 2H), 2.64 (s, 3H). $^{13}$C NMR: δ 169.5, 54.9, 26.1, 25.5.

(S)-2-amino-3-mercapto-N-methylpropanamide obtained above (7 mg, 0.052 mmol) was dissolved in 50 mM aqueous sodium phosphate buffer (pH 8, 2 mL). After the solution thus formed was degassed using argon, it was added to 6-(ethylamino)benzo[d]thiazole-2-carbonitrile (10 mg, 0.049 mmol) in 2 mL of degassed methanol. The reaction was stirred for 2 hours, and then diluted with sodium phosphate buffer and extracted with ethyl acetate (2×30 mL). The combined organic portions were washed with saturated aqueous NaCl solution (2 mL), dried (Na$_2$SO$_4$), and concentrated by evaporation. The residue was purified by flash chromatography on silica gel eluting with an ethyl acetate/hexane (1:1) mixture to afford Compound 7 as a yellow solid (12 mg, 80%). $^1$H NMR (400 MHz, CDCl$_3$): δ 7.89 (d, 1H, J=8.8 Hz), 6.97 (s, 1H), 6.81 (d, 1H, J=8.8 Hz), 6.73 (brs, 1H), 5.24 (t, 1H, J=10 Hz), 3.82-3.71 (m, 2H), 3.24 (q, 2H, J=7.2 Hz), 2.89 (d, 3H, J=4.4 Hz), 1.32 (t, 1H, J=7.2 Hz). $^{13}$C-NMR (100 MHz, CDCl$_3$): δ 171.5, 166.9, 154.8, 148.1, 146.1, 139.0, 125.5, 116.0, 101.3, 79.3, 38.9, 35.7, 26.5, 14.8.

EXAMPLE 8

Preparation of Compound 9: (S)-4,5-dihydro-2-(6,7-dihydro-5H-thiazolo[4,5-f]indol-2-yl)thiazole-4-carboxamide

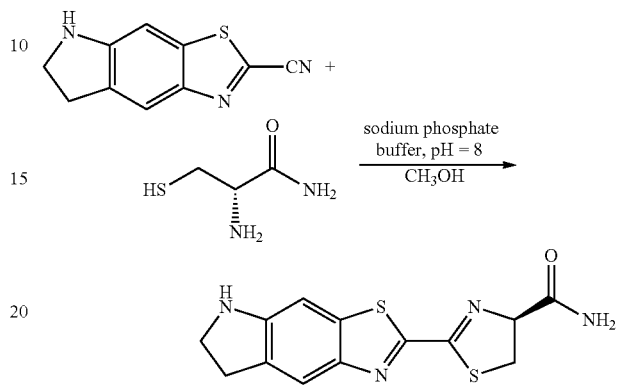

(S)-2-amino-3-mercaptopropanamide obtained in Example 1 (7 mg, 0.0596 mmol) was dissolved in 50 mM aqueous sodium phosphate buffer (pH 8, 2 mL). After the solution thus formed was degassed using argon, it was added to 6,7-dihydro-5H-thiazolo[4,5-f]indole-2-carbonitrile (10 mg, 0.049 mmol) in 2 ml of degassed methanol. The reaction mixture was stirred for 2 hours, and then diluted with sodium phosphate buffer and extracted with ethyl acetate (2×30 mL). The combined organic layers were washed with water (3×30 mL), dried (Na$_2$SO$_4$), filtered and concentrated to afford Compound 9 as a yellow solid (10 mg, 66%). $^1$H NMR (400 MHz, CDCl$_3$): δ 7.79 (s, 1H), 6.95 (s, 1H), 6.70 (brs, 1H), 5.61 (brs, 1H), 5.26 (t, 1H, J=12 Hz), 3.75 (m, 4H), 3.18 (t, 2H, J=8.0 Hz). $^{13}$C-NMR (100 MHz, CDCl$_3$): δ 173.3, 166.9, 154.5, 152.3, 147.2, 137.1, 131.8, 120.5, 98.6, 78.9, 47.9, 35.2, 29.3. HRMS (ESI$^+$) Calcd for C$_{13}$H$_{13}$N$_4$OS$_2$: 305.0531, Found: 305.0498.

EXAMPLE 9

Preparation of Compound 10: (S)-4,5-dihydro-2-(6,7-dihydro-5-methyl-5H-thiazolo[4,5-f]indol-2-yl)thiazole-4-carboxamide Compound 10 was prepared as a yellow solid (12 mg, 81%) in a manner similar to that described in Example 8 using suitable starting materials. $^1$H NMR (400 MHz, CDCl$_3$): δ 7.71 (s, 1H), 6.71 (s, 1H), 6.70 (brs, 1H), 5.68 (brs, 1H), 5.25 (t, 1H, J=9.2 Hz), 3.75 (d, 2H, J=10.0 Hz), 3.51 (t, 2H, J=8.0 Hz), 3.10 (t, 2H, J=8.0 Hz), 2.86 (s, 3H). $^{13}$C-NMR (100 MHz, CDCl$_3$): δ 173.5, 166.8, 153.7, 153.6, 146.5, 137.7, 132.9, 120.0, 96.1, 78.9, 55.8, 35.26, 35.18, 28.2. HRMS (ESI$^+$) Calcd for C$_{14}$H$_{15}$N$_4$OS$_2$: 319.0687, Found: 319.0677.

EXAMPLE 10

Preparation of Compound 14: (S)-2-(5,6,7,8-tetrahydrothiazolo[4,5-g]quinolin-2-yl)-4,5-dihydrothiazole-4-carboxamide (S)-2-amino-3-mercaptopropanamide obtained in Example 1 (7 mg, 0.0596 mmol) was dissolved in a 50 mM aqueous sodium phosphate buffer (pH 8, 2 mL). After the solution was degassed using argon, it was added to 5,6,7,8-tetrahydrothiazolo[4,5-g]quinoline-2-carbonitrile (10 mg, 0.046 mmol) in 2 mL of degassed methanol. The reaction mixture was stirred for 2 hours, diluted with a sodium phosphate buffer, and extracted with ethyl acetate (2×30 mL). The combined organic layers were washed with water (3×30 mL), dried ($Na_2SO_4$), filtered, and concentrated. The crude compound was purified by flash chromatography on silica gel eluting with an ethyl acetate/hexane (6:4) mixture to afford Compound 14 as a yellow solid (10 mg, 67%). $^1$H NMR (400 MHz, $CDCl_3$): δ 7.68 (s, 1H), 6.82 (s, 1H), 6.69 (brs, 1H), 5.51 (brs, 1H), 5.25 (t, 1H, J=9.6 Hz), 4.32 (brs, 1H) 3.75 (d, 2H, J=9.6 Hz), 3.39 (t, 2H, J=6.0 Hz), 2.92 (t, 2H, J=6.8 Hz), 1.97 (m, 2H). $^{13}$C-NMR (100 MHz, $CDCl_3$): δ 173.3, 166.9, 154.1, 145.9, 145.5, 136.3, 124.8, 123.2, 102.9, 78.9, 42.1, 35.2, 27.8, 21.7. HRMS (ESI$^+$) Calcd for $C_{14}H_{15}N_4OS_2$: 319.0687, Found: 319.0698.

EXAMPLE 11

Preparation of Compound 20: (S)-2-(8,8-dimethyl-5,6,7,8-tetrahydrothiazolo[4,5-g]quinolin-2-yl)-4,5-dihydrothiazole-4-carboxamide

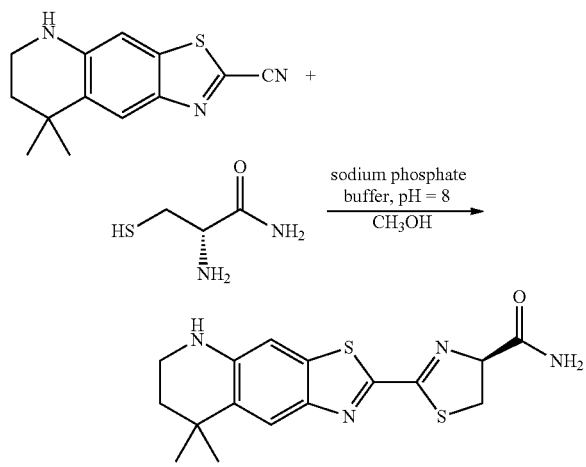

(S)-2-amino-3-mercaptopropanamide obtained in Example 1 (11.7 mg, 0.098 mmol) was dissolved in 3 mL of a 50 mM aqueous sodium phosphate buffer (pH 8). After the solution was degassed under argon, it was added to 8,8-dimethyl-5,6,7,8-tetrahydrothiazolo[4,5-g]quinoline-2-carbonitrile (20 mg, 0.082 mmol) in 3 mL of degassed methanol. The reaction mixture was stirred for 1 hour, diluted with a sodium phosphate buffer (5 mL), and extracted with ethyl acetate (2×20 mL). The combined organic layers were washed with water (3×30 mL), dried with $Na_2SO_4$, filtered, and concentrated under reduced pressure. The crude compound was purified by flash chromatography on silica gel using 2% methanol/dichloromethane to afford Compound 20 as an orange solid (15 mg, 52%). $^1$H NMR (400 MHz, $CDCl_3$): δ 7.96 (s, 1H), 6.82 (s, 1H), 6.70 (br s, 1H), 5.73 (br s, 1H), 5.26 (t, 1H, J=9.6 Hz), 3.76 (d, 2H, J=10.0 Hz), 3.41 (t, 2H, J=6.0 Hz), 1.77 (t, 2H, J=5.6 Hz), 1.35 (s, 6H). HRMS (ESI$^+$) Calcd for $C_{16}H_{19}N_4OS_2$: 347.1000, Found: 347.0964.

EXAMPLE 12

Preparation of Compound 21: (S)-2-(5,8,8-trimethyl-5,6,7,8-tetrahydrothiazolo[4, 5-g]quinolin-2-yl)-4,5-dihydrothiazole-4-carboxamide

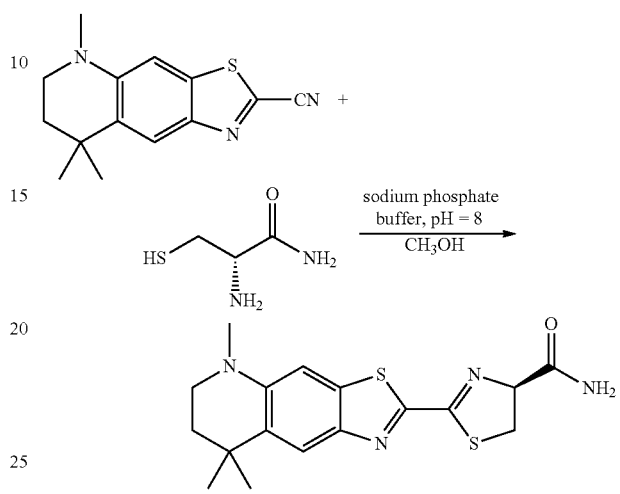

(S)-2-amino-3-mercaptopropanamide obtained in Example 1 (11.2 mg, 0.093 mmol) was dissolved in 3 mL of a 50 mM aqueous sodium phosphate buffer (pH 8). After the solution was degassed using argon, it was added to 5,8,8-trimethyl-5,6,7,8-tetrahydrothiazolo[4,5-g]quinoline-2-carbonitrile (20 mg, 0.077 mmol) in 3 mL of degassed methanol. The reaction mixture was stirred for 1 hour, diluted with a sodium phosphate buffer (5 mL), and extracted with ethyl acetate (2×20 mL). The combined organic layers were washed with water (3×30 mL), dried with $Na_2SO_4$, filtered, and concentrated under reduced pressure. The crude compound was purified by flash chromatography on silica gel using 2% methanol/dichloromethane to afford Compound 21 as an orange solid (12 mg, 43%). $^1$H NMR (400 MHz, $CDCl_3$): δ 7.93 (s, 1H), 6.87 (s, 1H), 6.71 (br s, 1H), 5.52 (br s, 1H), 5.26 (t, 1H, J=9.6 Hz), 3.77 (d, 2H, J=9.6 Hz), 3.40 (t, 2H, J=6.0 Hz), 3.02 (s, 3H), 1.79 (t, 2H, J=6.4 Hz), 1.34 (s, 6H). HRMS (ESI$^+$) Calcd for $C_{17}H_{21}N_4OS_2$: 361.1157, Found: 347.1138.

EXAMPLE 13

Preparation of Compound 22: (S)-2-(6,7,8,9-tetrahydrothiazolo[5,4-f]quinolin-2-yl)-4,5-dihydrothiazole-4-carboxamide

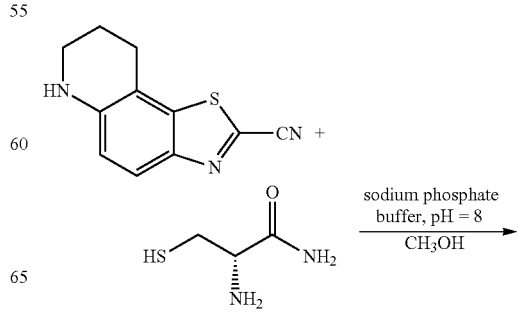

-continued

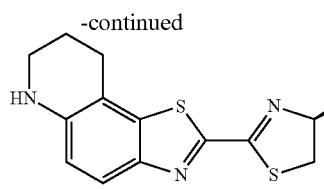

(S)-2-amino-3-mercaptopropanamide obtained in Example 1 (13 mg, 0.11 mmol) was dissolved in 3 mL of a 50 mM aqueous sodium phosphate buffer (pH 8). After the solution was degassed under argon, it was added to 6,7,8,9-tetrahydrothiazolo[5,4-f]quinoline-2-carbonitrile (20 mg, 0.09 mmol) in 3 mL of degassed methanol. The reaction mixture was stirred for 1 hour, diluted with a sodium phosphate buffer (5 mL), and extracted with ethyl acetate (2×20 mL). The combined organic layers were washed with water (3×30 mL), dried with $Na_2SO_4$, filtered, and concentrated under reduced pressure. The crude compound was purified by flash chromatography on silica gel using 2% methanol/dichloromethane to afford Compound 22 as an orange solid (13 mg, 45%). $^1$H NMR (400 MHz, $CDCl_3$): δ 7.75 (d, 1H, J=9.2 Hz), 6.69 (d, 1H, J=8.4 Hz), 6.68 (br s, 1H), 5.49 (br s, 1H), 5.27 (t, 1H, J=9.6 Hz), 3.78 (d, 2H, J=9.6 Hz), 3.39 (t, 2H, J=5.2 Hz), 2.81 (t, 2H, J=6.0 Hz), 2.06-2.12 (m, 2H). HRMS (ESI$^+$) Calcd for $C_{14}H_{15}N_4OS_2$: 319.0687, Found: 319.0668.

EXAMPLE 14

Preparation of Compound 23: (S)-2-(6-methyl-6,7,8,9-tetrahydrothiazolo[5,4-f]quinolin-2-yl)-4,5-dihydrothiazole-4-carboxamide

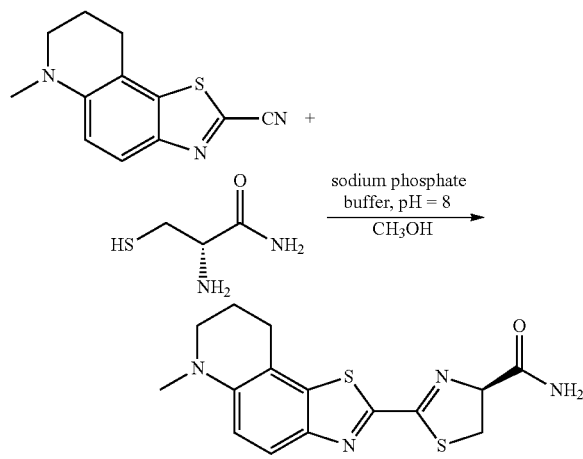

(S)-2-amino-3-mercaptopropanamide obtained in Example 1 (6.2 mg, 0.052 mmol) was dissolved in 2 mL of a 50 mM aqueous sodium phosphate buffer (pH 8). After the solution was degassed under argon, it was added to 6-methyl-6,7,8,9-tetrahydrothiazolo[5,4-f]quinoline-2-carbonitrile (10 mg, 0.043 mmol) in 2 mL of degassed methanol. The reaction mixture was stirred for 1 hour, diluted with a sodium phosphate buffer (5 mL), and extracted with ethyl acetate (2×10 mL). The combined organic layers were washed with water (3×20 mL), dried with $Na_2SO_4$, filtered, and concentrated under reduced pressure. The crude compound was purified by flash chromatography on silica gel using 2% methanol/dichloromethane to afford Compound 23 as an orange solid (5 mg, 35%). $^1$H NMR (400 MHz, $CDCl_3$): δ 7.78 (d, 1H, J=9.2 Hz), 6.83 (d, 1H, J=9.2 Hz), 6.65 (br s, 1H), 5.45 (br s, 1H) 5.21 (t, 1H, J=10.0 Hz), 3.71 (d, 2H, J=9.6 Hz), 3.27 (t, 2H, J=5.6 Hz), 2.94 (s, 3H), 2.76 (t, 2H, J=6.4 Hz), 2.04-2.07 (m, 2H).

EXAMPLE 15

Preparation of Compound 25: (S)-4,5-dihydro-2-(6-hydroxybenzo thiazol-2-yl)thiazole-4-carboxamide

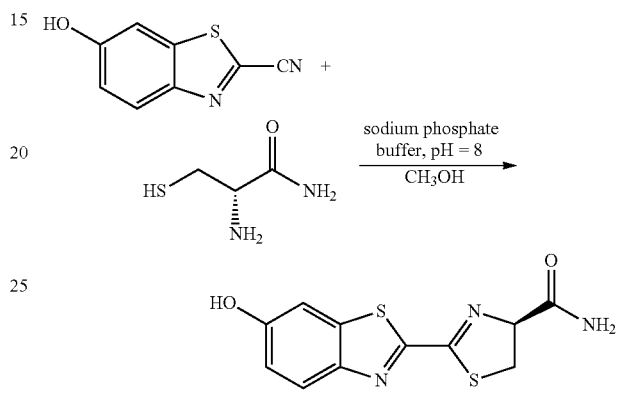

(S)-2-amino-3-mercaptopropanamide obtained in Example 1 (8 mg, 0.066 mmol) was dissolved in 50 mM aqueous sodium phosphate buffer (pH 8, 2 mL). After the solution was degassed using argon, it was added to 6-hydroxybenzo[d]thiazole-2-carbonitrile (10 mg, 0.056 mmol) in 2 ml of degassed methanol. The reaction mixture was stirred for 2 hours, and then diluted with sodium phosphate buffer and extracted with ethyl acetate (2×30 mL). The combined organic layers were washed with water (3×30 mL), dried ($Na_2SO_4$), filtered, and concentrated to afford Compound 25 as a yellow solid (13 mg, 82%). $^1$H NMR (400 MHz, DMSO-$d_6$): δ 7.94 (d, 1H, J=8.8 Hz), 7.43 (s, 1H), 7.04 (dd, 1H, J=2.4, 9.2 Hz), 5.38 (t, 1H, J=10.0 Hz), 3.61-3.76 (m, 2H). $^{13}$C NMR (100 MHz, $CDCl_3$): δ 171.8, 164.6, 158.0, 157.5, 146.9, 137.9, 125.5, 117.7, 107.4, 79.7, 35.1. HRMS (ESI$^+$) Calcd for $C_{11}H_{10}N_3O_2S_2$: 280.0215, Found: 280.0188.

EXAMPLE 16

Preparation of Compound 26: (S)-2-(6-methoxybenzo[d]thiazol-2-yl)-4,5-dihydrothiazole-4-carboxamide

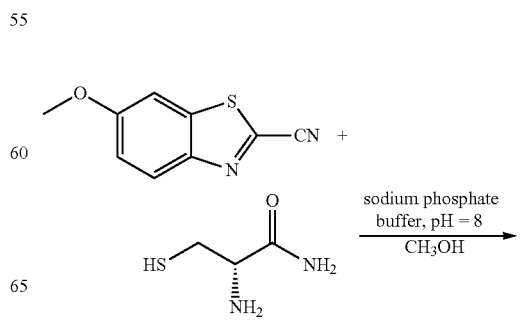

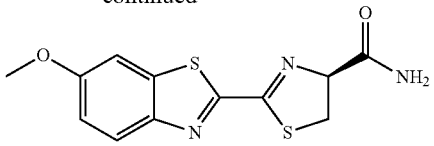

(S)-2-amino-3-mercaptopropanamide obtained in Example 1 (7.5 mg, 0.063 mmol) was dissolved in a 50 mM aqueous sodium phosphate buffer (pH 8, 2 mL). After the solution was degassed using argon, it was added to 6-methoxybenzo[d]thiazole-2-carbonitrile (10 mg, 0.052 mmol) in 2 mL of degassed methanol. The reaction mixture was stirred for 2 hours, and then diluted with a sodium phosphate buffer and extracted with ethyl acetate (2×30 mL). The combined organic layers were washed with water (3×30 mL), dried ($Na_2SO_4$), filtered, and concentrated. The crude compound was purified by flash chromatography on silica gel eluting with an ethyl acetate/hexane (6:4) mixture to afford Compound 26 as a white solid (13 mg, 85%). $^1$H NMR (400 MHz, $CDCl_3$): δ 8.03 (d, 1H, J=9.2 Hz), 7.34 (d, 1H, J=2.8 Hz), 7.14 (dd, 1H, J=2.4, 8.8 Hz), 6.68 (brs, 1H), 5.72 (brs, 1H) 5.29 (t, 1H, J=9.6 Hz), 3.90 (s, 3H) 3.80 (d, 2H, J=9.6 Hz). $^{13}$C NMR (100 MHz, $CDCl_3$): δ 173.0, 166.8, 159.5, 157.7, 148.0, 137.8, 125.6, 117.2, 103.9, 79.1, 56.0, 35.2. HRMS ($ESI^+$) Calcd for $C_{12}H_{12}N_3O_2S_2$: 294.0371, Found: 294.0332.

EXAMPLE 17

Preparation of Compound 27: (S)-2-(6-(benzyloxy)benzo[d]thiazol-2-yl)-4,5-dihydrothiazole-4-carboxamide

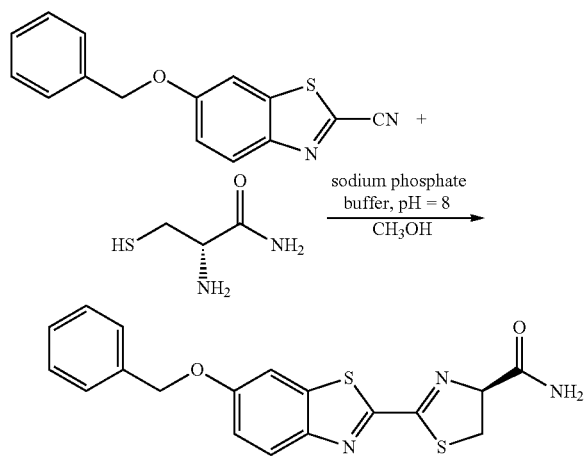

(S)-2-amino-3-mercaptopropanamide obtained in Example 1 (8.0 mg, 0.066 mmol) was dissolved in a 50 mM aqueous sodium phosphate buffer, (pH 8, 2 mL). After the solution was degassed using argon, it was added to 6-(benzyloxy)benzo[d]thiazole-2-carbonitrile (10 mg, 0.037 mmol) in 2 mL of degassed methanol. The reaction mixture was stirred for 2 hours, and then diluted with a sodium phosphate buffer and extracted with ethyl acetate (2×30 mL). The combined organic layers were washed with water (3×20 mL), dried ($Na_2SO_4$), filtered and concentrated. The crude compound was purified by flash chromatography on silica gel eluting with an ethyl acetate/hexane (6:4) mixture to afford the Compound 27 as a white solid (12 mg, 86%). $^1$H NMR (400 MHz, $CDCl_3$): δ 8.04 (d, 1H, J=9.2 Hz), 7.33-7.47 (m, 6H), 7.22 (dd, 1H, J=2.8, 8.8 Hz), 6.67 (br s, 1H), 5.64 (br s, 1H) 5.29 (t, 1H, J=9.6 Hz), 5.15 (s, 2H) 3.79 (d, 2H, J=9.6 Hz). $^{13}$CNMR (100 MHz, $CDCl_3$): δ 172.9, 166.8, 158.7, 157.9, 148.2, 137.8, 136.3, 128.9, 128.5, 127.7, 125.7, 117.7, 105.1, 79.1, 70.8, 35.2. HRMS ($ESI^+$) Calcd for $C_{18}H_{15}N_3O_2S_2Na$: 392.0504, Found: 392.0489.

EXAMPLE 18

Preparation of Compound 28: (S)-2-(benzo[d]thiazol-2-yl)-4,5-dihydrothiazole-4-carboxamide (S)-2-amino-3-mercaptopropanamide obtained in Example 1 (9 mg, 0.748 mmol) was dissolved in a 50 mM aqueous sodium phosphate buffer (pH 8, 2 mL). After the solution was degassed using argon, it was added to benzo[d]thiazole-2-carbonitrile (10 mg, 0.062 mmol) in 2 mL of degassed methanol. The reaction mixture was stirred for 2 hours, and then diluted with a sodium phosphate buffer and extracted with ethyl acetate (2×30 mL). The combined organic layers were washed with water (3×30 mL), dried ($Na_2SO_4$), filtered, and concentrated. The crude compound was purified by flash chromatography on silica gel eluting with an ethyl acetate/hexane (7:3) mixture to afford Compound 28 as a white solid (13 mg, 79%). $^1$H NMR (400 MHz, $CDCl_3$): δ 8.16 (d, 1H, J=8.4 Hz), 7.94 (d, 1H, J=8.4 Hz), 7.49-7.57 (m, 2H), 6.70 (brs, 1H), 5.85 (brs. 1H), 5.31 (t, 1H, J=9.6 Hz), 3.81 (d, 2H, J=9.6 Hz). $^{13}$C-NMR (100 MHz, $CDCl_3$): δ 173.0, 166.9, 160.5, 153.4, 136.0, 127.5, 127.1, 125.0, 122.1, 79.1, 35.2. HRMS ($ESI^+$) Calcd for $C_{11}H_9N_3OS_2Na$: 286.0085, Found: 286.0067.

EXAMPLE 19

Preparation of Compound 29: (S)-2-(6-(isopropylamino)benzo[d]thiazol-2-yl)-N-methyl-4,5-dihydrothiazole-4-carboxamide

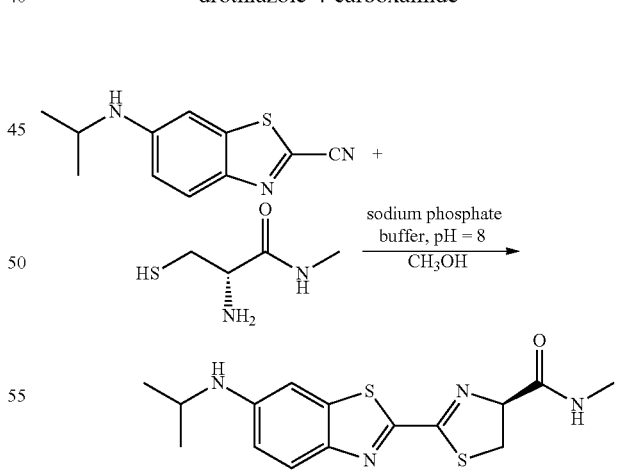

(S)-2-amino-3-mercapto-N-methylpropanamide obtained in Example 7 above (9 mg, 0.067 mmol) was dissolved in a 50 mM aqueous sodium phosphate buffer (pH 8, 2 mL). After the solution was degassed using argon, it was added to 6-(isopropylamino)benzo[d]thiazole-2-carbonitrile (10 mg, 0.046 mmol) in 2 mL of degassed methanol. After the reaction mixture was stirred for 2 hours, it was diluted with a sodium phosphate buffer and extracted with ethyl acetate (2×30 mL). The combined organic portions were washed with a saturated aqueous NaCl solution (2 mL), dried (Na₂SO₄), and concentrated. The residue was purified by flash chromatography on silica gel eluting with ethyl acetate/hexanes (7:3) mixture to afford Compound 2 as a yellow solid (13 mg, 84%). ¹H NMR (400 MHz, CDCl₃): δ 7.86 (d, 1H, J=8.8 Hz), 6.92 (d, 1H, J=2.4 Hz), 6.75 (dd, 1H, J=9.2, 2.4 Hz), 6.73 (brs, 1H), 5.23 (t, 1H, J=9.6 Hz), 3.66-3.81 (m, 3H), 2.89 (d, 3H, J=5.2 Hz), 1.26 (d, 6H, J=6.4 Hz). ¹³C-NMR (100 MHz, CDCl₃): δ 171.5, 166.9, 154.5, 147.4, 145.7, 139.1, 125.5, 116.1, 101.3, 79.2, 44.6, 35.7, 26.4, 23.0. ESI-MS (MH+): 335.1.

EXAMPLE 20

Preparation of Compound 30: (S)-2-(6-(dimethylamino)benzo[d]thiazol-2-yl)-N-(2-hydroxyethyl)-4,5-dihydrothiazole-4-carboxamide

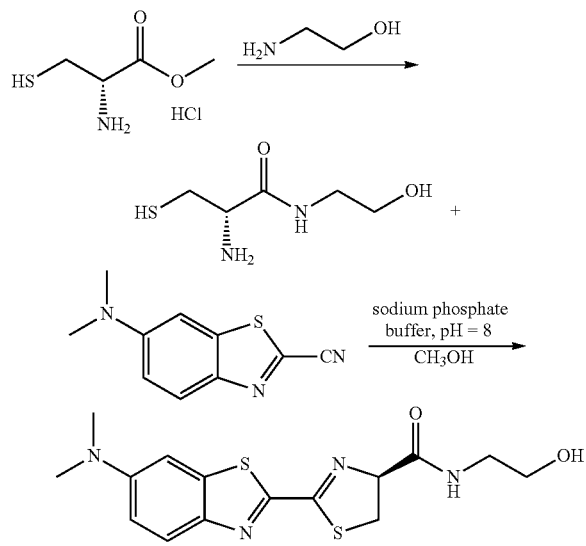

D-Cysteine methyl ester hydrochloride (100 mg, 0.582 mmol) was dissolved in ethanolamine (1 mL). The mixture was stirred at room temperature for 2 hours. Mass spectrometry indicated formation of D-Cysteine ethanolamide and disulfide (1:1). This crude material was directly used in the next step without further purification.

Crude D-Cysteine ethanolamide obtained above (12 mg, 0.073 mmol) was dissolved in a 50 mM aqueous sodium phosphate buffer (pH 8, 2 mL). After the solution was degassed using argon, it was added to 6-(dimethylamino)benzo[d]thiazole-2-carbonitrile (10 mg, 0.049 mmol) in 2 mL of degassed methanol. After the reaction mixture was stirred for 2 hours, it was diluted with a sodium phosphate buffer and extracted with ethyl acetate (2×30 mL). The combined organic portions were washed with a saturated aqueous NaCl solution (2 mL), dried (Na₂SO₄), and concentrated. The residue was purified by flash chromatography on silica gel eluting with ethyl acetate/methanol (95:5) mixture to afford Compound 30 as a yellow solid (11 mg, 63%). ¹H NMR (400 MHz, CDCl₃): δ 7.96 (d, 1H, J=9.2 Hz), 7.17 (brs, 1H), 7.0 (brs, 1H), 7.0 (d, 1H, J=9.2 Hz), 5.27 (t, 1H, J=9.6 Hz), 3.66-3.82 (m, 4H), 3.52 (m, 2H), 3.08 (s, 6H). ESI-MS (MH+): 351.1.

EXAMPLE 21

Preparation of Compound 31: (S)-2-(6,7-dihydro-5H-thiazolo[4,5-f]indol-2-yl)-N-methyl-4,5-dihydrothiazole-4-carboxamide

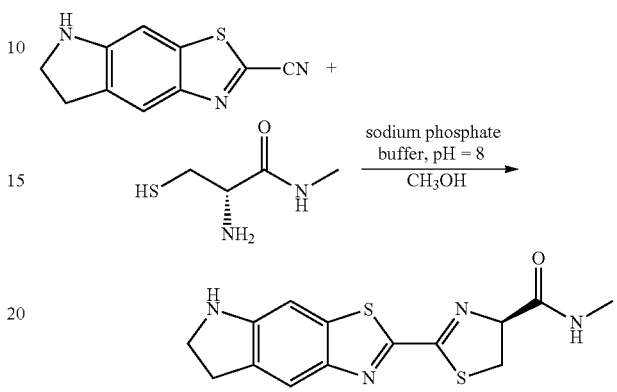

(S)-2-amino-3-mercapto-N-methylpropanamide obtained in Example 7 above (8 mg, 0.059 mmol) was dissolved in 2 mL of a 50 mM aqueous sodium phosphate buffer (pH 8). After the solution was degassed under argon, it was added to 6,7-dihydro-5H-thiazolo[4,5-f]indole-2-carbonitrile (10 mg, 0.049 mmol) in 2 ml of degassed methanol. After the reaction mixture was stirred for 1 hour, it was diluted with a sodium phosphate buffer (5 mL) and extracted with ethyl acetate (2×20 mL). The combined organic layers were washed with water (2×20 mL), dried with Na₂SO₄, filtered, and concentrated under reduced pressure. The crude product was purified by flash chromatography on silica gel using an ethyl acetate:hexane (6:4) mixture to afford Compound 31 as an orange solid (8.4 mg, 54%). ¹H NMR (400 MHz, CDCl₃): δ 7.79 (s, 1H), 6.97 (s, 1H), 6.74 (br s, 1H), 5.23 (t, 1H, J=9.6 Hz), 3.75 (m, 4H), 3.18 (t, 2H, J=7.4 Hz), 2.89 (d, 3H, J=4.8 Hz). ESI-MS (M+H): 319.1.

EXAMPLE 22

Preparation of Compound 32: (S)—N-methyl-2-(5-methyl-6,7-dihydro-5H-thiazolo[4,5-f]indol-2-yl)-4,5-dihydrothiazole-4-carboxamide

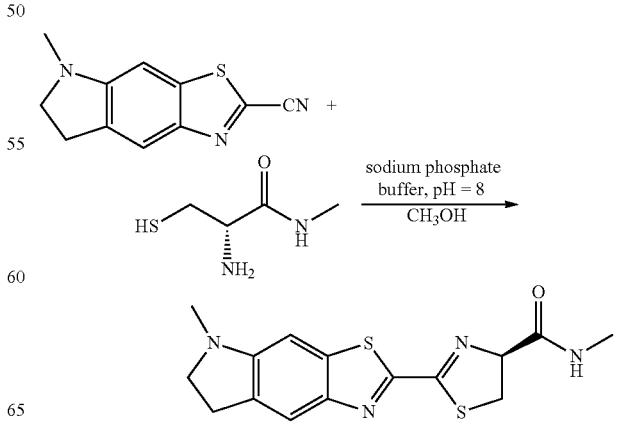

(S)-2-amino-3-mercapto-N-methylpropanamide obtained in Example 7 above (8.9 mg, 0.066 mmol) was dissolved in 2 mL of a 50 mM aqueous sodium phosphate buffer (pH 8). After the solution was degassed under argon, it was added to 5-methyl-6,7-dihydro-5H-thiazolo[4,5-f]indole-2-carbonitrile (12 mg, 0.055 mmol) in 2 ml of degassed methanol. After the reaction was stirred for 1 hour, it was diluted with a sodium phosphate buffer (5 mL) and extracted with ethyl acetate (2×20 mL). The combined organic layers were washed with water (2×20 mL), dried with $Na_2SO_4$, filtered, and concentrated under reduced pressure. The crude compound was purified by flash chromatography on silica gel using an ethyl acetate:hexane (6:4) mixture to afford Compound 32 as an orange solid (3 mg, 17%). $^1$H NMR (400 MHz, $CDCl_3$): δ 7.72 (s, 1H), 6.74 (br s, 1H), 6.73 (s, 1H), 5.68 (brs, 1H), 5.23 (t, 1H, J=9.6 Hz), 3.85-3.65 (m, 2H), 3.52 (t, 2H, J=8.0 Hz), 3.11 (t, 2H, J=8.0 Hz), 2.90 (d, 3H, J=4.8 Hz), 2.87 (s, 3H). ESI-MS (M+H): 333.4.

EXAMPLE 23

In Vitro Assays

General Procedures

Recombinant FAAH, FAAH assay buffer, and FAAH inhibitors URB-597, PF-750, and PF-3845 were purchased from Cayman Chemical.

Bioluminescence Imaging

Bioluminescence assays were performed in either a Turner Veritas luminometer or a Xenogen IVIS-100 imaging system. For Veritas experiments, white 96-well plates were used (Costar 3912). For IVIS experiments, black 96-well plates were used (Costar 3915).

In Vitro FAAH Assay

Luciferin amides (50 μM) were treated with FAAH and FAAH buffer (Cayman Chemical) in the presence or absence of 50 μM FAAH inhibitor URB-597 or 50 μM luciferase inhibitor 2-(4'-methoxyphenyl)benzothiazole. After 10 minutes at room temperature, R218K mutant firefly luciferase was added at a concentration of 3 μg/mL and bioluminescence was detected on a Turner Veritas luminometer.

Cell Culture

Chinese hamster ovary-K1 (CHO-K1) cells were grown in a $CO_2$ incubator at 37° C. with 5% $CO_2$ and were cultured in F-12K Nutrient Mixture (GIBCO) supplemented with 10% fetal bovine serum and 100 U/mL penicillin/streptomycin.

Transfections

Wild-type and $R_{218}K$ mutant luciferases were cloned into the BamHI-NotI site of pCDNA 3.1 and transiently transfected into CHO-K1 cells with Lipofectamine 2000 in 96-well tissue culture-treated plates for intact cell assays, or 6-well plates for lysed cell assays. For intact cells, 0.075 μg plasmid/well was transfected; for lysed cells, 2.25 μg plasmid/well was transfected.

Intact Cell FAAH Assays

Medium was removed from transfected CHO cells and replaced with 60 μL Optimem with or without a FAAH inhibitor (10 μM). The cells were incubated for one hour in the $CO_2$ incubator at 37° C. Cells were then washed with Hank's balanced salt solution (HBSS) and overlaid with 60 μL a luciferin amide substrate in HBSS. Imaging assays were performed 3 minutes after substrate addition, with final substrate concentrations ranging from 0.122 to 250 μM.

Lysed Cell FAAH Assays

Medium was removed from transfected CHO cells and the cells were overlaid with 2 mL Optimem with or without a FAAH inhibitor (10 μM). The cells were incubated for one hour in the $CO_2$ incubator at 37° C. Cells were then washed with HBSS and lysed for 10 minutes at room temperature with 1 mL 1× passive lysis buffer (Promega) per well. Cells from one and a half wells of a 6-well plate were used to test one luciferin amide substrate in triplicate at 12 concentrations. Luminescence assays were initiated by adding 30 μL 2× substrate in buffer (20 mM Tris (pH 7.4), 0.1 mM EDTA, 8 mM $MgSO_4$, 4 mM ATP, 6 mg/mL BSA, 33 mM DTT, and 250 μM Coenzyme A) to 30 μL of lysate in a 96-well plate. Imaging assays were performed 3 minutes after substrate addition, with final substrate concentrations ranging from 0.122 to 250 μM.

Results and Discussion

Generation of Bioluminescence by Luciferin Amides and its Inhibition:

Four luciferin amides (50 μM), i.e., Compounds 1, 9, 10, and 25, were treated with a buffer alone, a buffer containing FAAH, a buffer containing FAAH+50 μM URB-597 (i.e., a FAAH inhibitor), or a buffer containing FAAH+50 μM luciferase inhibitor 2-(4'-methoxyphenyl)benzothiazole. After 10 minutes at room temperature, R218K luciferase was added at a concentration of 3 μg/mL and bioluminescence was detected on a Turner Veritas. The results are summarized in FIG. 1. As shown in FIG. 1, addition of FAAH caused a large increase in bioluminescence signal versus buffer (269-fold for Compound 25, 167-fold for Compound 1, 8972-fold for Compound 9, and 139-fold for Compound 10). These bioluminescence signals were inhibited by more than 100-fold by treatment with the FAAH inhibitor URB-597. Further, addition of the luciferase inhibitor 2-(4'-methoxyphenyl)benzothiazole resulted in 14.5-fold inhibition of the signal generated from Compound 25, and only 2.3-fold inhibition of the signal generated from Compound 9. These results show that luciferin amides were effective in generating bioluminescence in the presence of FAAH and luciferase. The bioluminescence could be inhibited by a FAAH inhibitor, suggesting that luciferin amides were converted to luciferins by FAAH. In addition, bioluminescence generated by certain luciferin amides were not significantly inhibited by a luciferase inhibitor.

Figure 2:
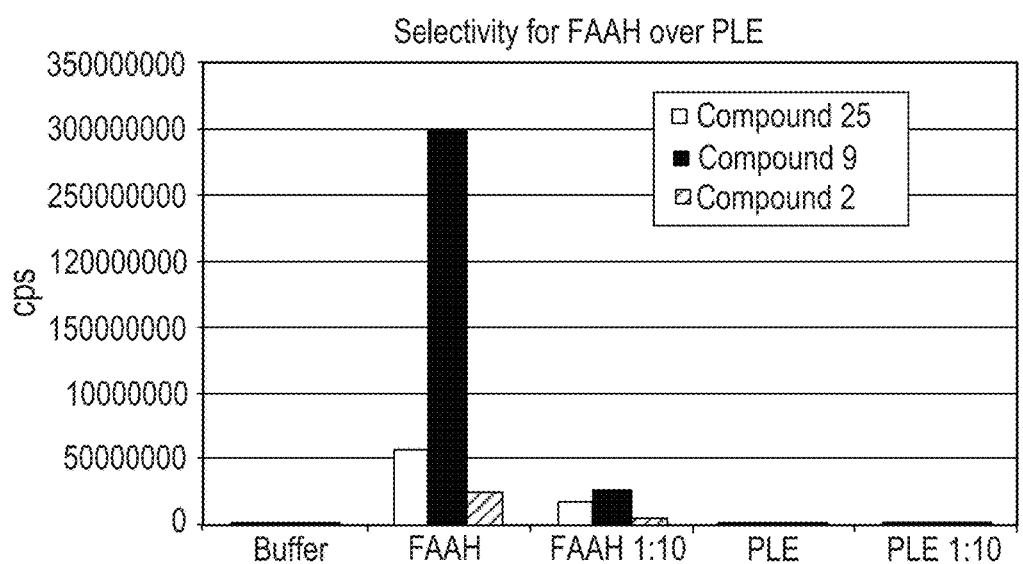
FIG. 2 is a graph illustrating that certain exemplary luciferin amides were selectively converted to their corresponding luciferins by FAAH.

Conversion of Luciferin Amides to Luciferins by FAAH:

Three luciferin amides (50 μM), i.e., Compounds 2, 9, and 25, were treated with a buffer alone, a buffer containing FAAH, a buffer containing FAAH 1:10 (i.e., a ten-fold dilution of FAAH), a buffer containing pig liver esterase (PLE), or a buffer containing PLE 1:10 (i.e., a ten-fold dilution of PLE). After one hour at room temperature, R218K luciferase was added at a concentration of 3 μg/mL and bioluminescence was detected on a Turner Veritas. The results are summarized in FIG. 2. As shown in FIG. 2, treatment with PLE at both concentrations failed to elicit a bioluminescence signal. In addition, dilution of the FAAH enzyme concentration resulted in a corresponding reduction in the intensity of the bioluminescent signal.

Figure 3:
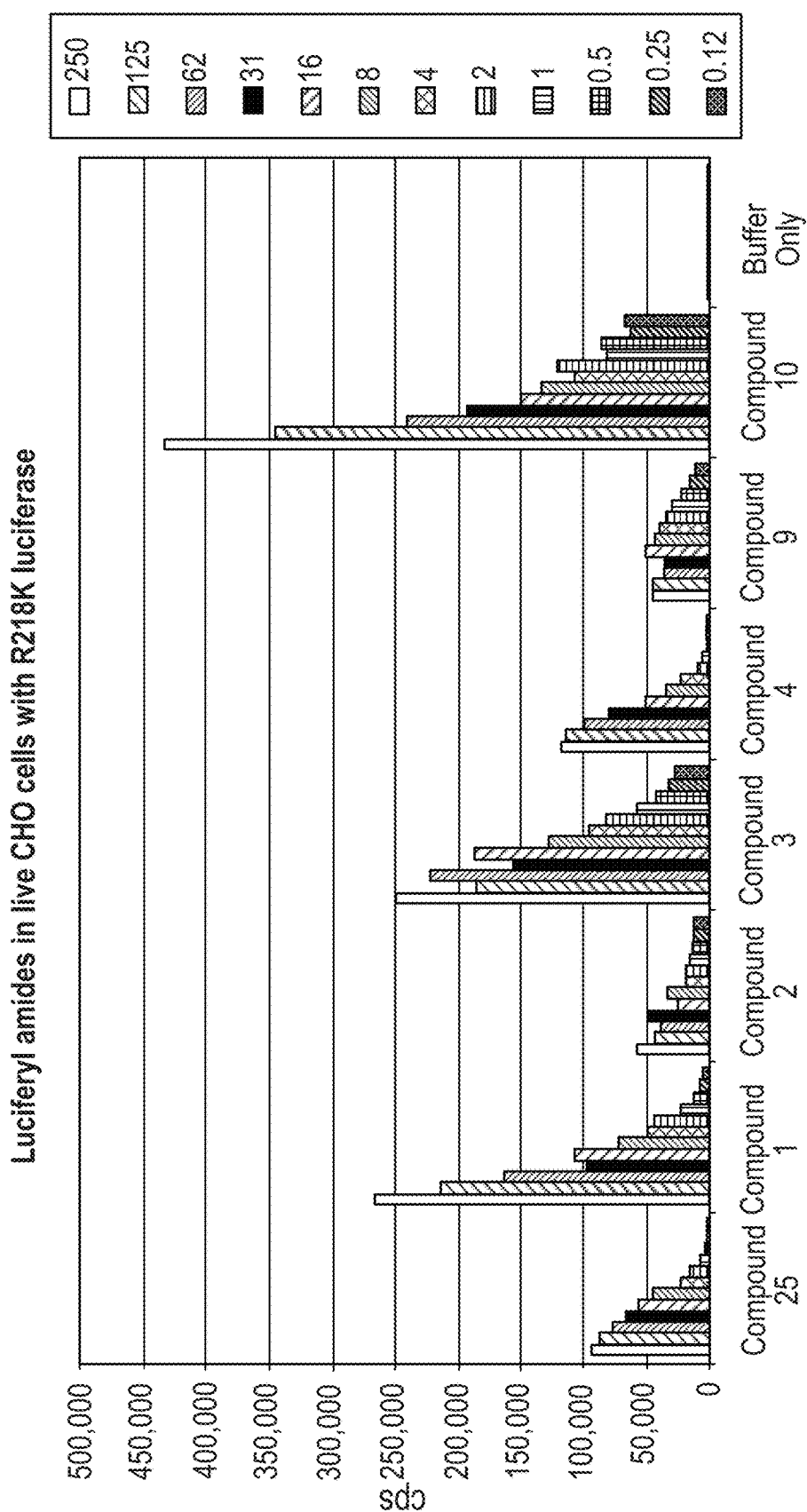
FIG. 3 is a graph illustrating that certain exemplary luciferin amides generated bioluminescence in live CHO cells expressing R218K luciferase.

Light Emission from Live CHO Cells:

Seven luciferin amides, i.e., Compounds 1-4, 9, 10, and 25, were tested in live CHO cells expressing R218K luciferase at various concentrations (i.e., 0.12 μM, 0.25 μM, 0.5 μM, 1 μM, 2 μM, 4 μM, 8 μM, 16 μM, 31 μM, 62 μM, 125 μM, and 250 μM). The results are summarized in FIG. 3. As shown in FIG. 3, all of the tested luciferin amides generated bioluminescence in live CHO cells expressing R218K luciferase at all tested concentration levels, suggesting that the tested luciferin amides were cell-permeable, and were converted to their respective light-emitting luciferin substrates in live CHO cells.

Figure 4:
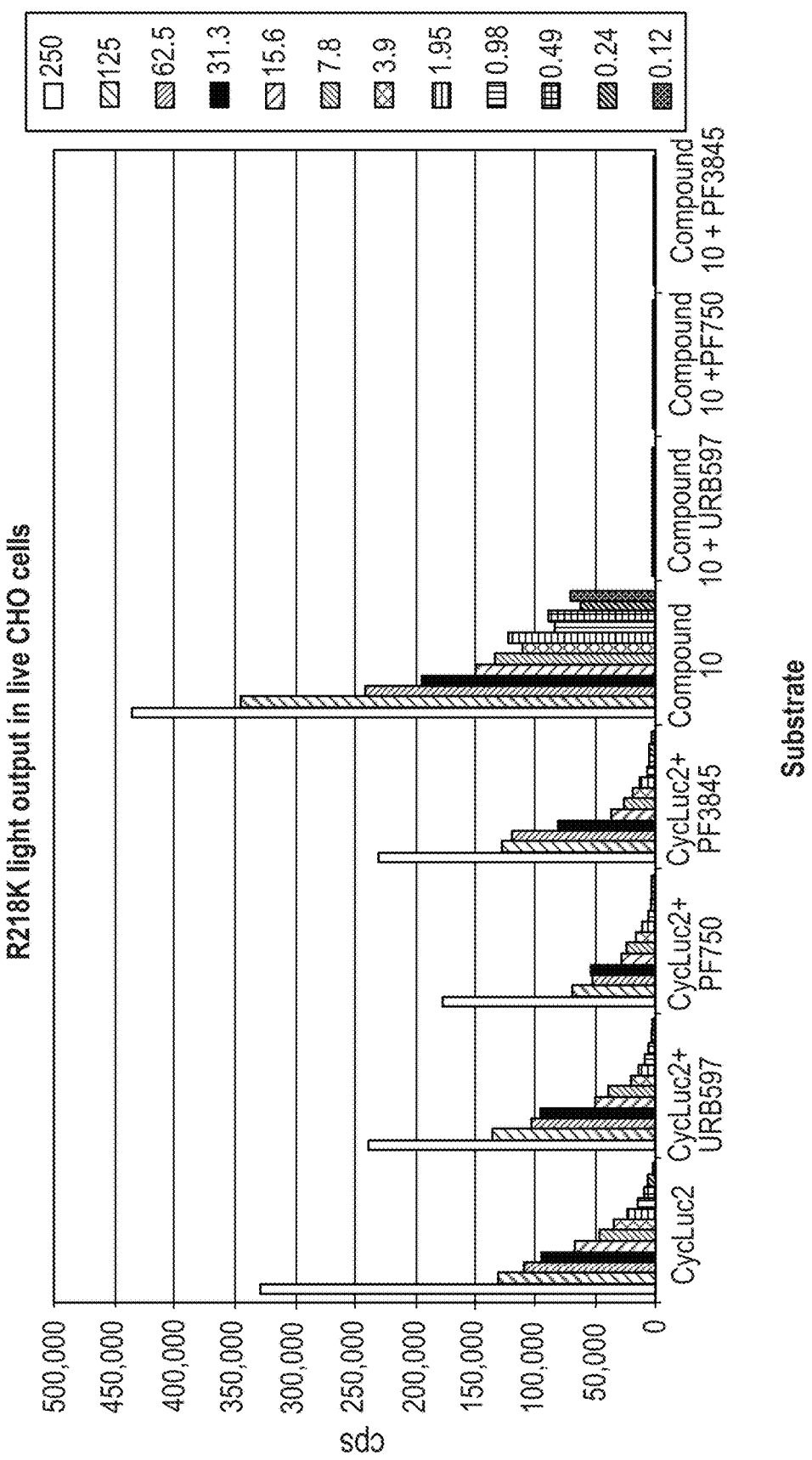
FIG. 4 is a graph illustrating in vitro detection of FAAH activity in live CHO cells by using an exemplary luciferin amide and its corresponding luciferin in the presence or absence of a FAAH inhibitor.

Further, Compound 10 and its corresponding luciferin (i.e., CycLuc2) were tested in live CHO cells expressing R218K luciferase at various concentrations (i.e., 0.12 µM, 0.24 µM, 0.49 µM, 0.98 µM, 1.95 µM, 3.9 µM, 7.8 µM, 15.6 µM, 31.3 µM, 62.5 µM, 125 µM, and 250 µM) in the presence of 50 µM of the FAAH inhibitors URB-597, PF-750, and PF-3845. The results are summarized in FIG. 4. As shown in FIG. 4, Compound 10 resulted in greater light emission than its corresponding luciferin at all concentrations tested. In addition, treatment with FAAH inhibitors URB-597, PF-750, and PF-3845 had no significant effect on light output generated from Compound 10's corresponding luciferin, but resulted in complete inhibition of light output from Compound 10, suggesting FAAH as the enzyme that converted Compound 10 into its corresponding luciferin.

Figure 5:
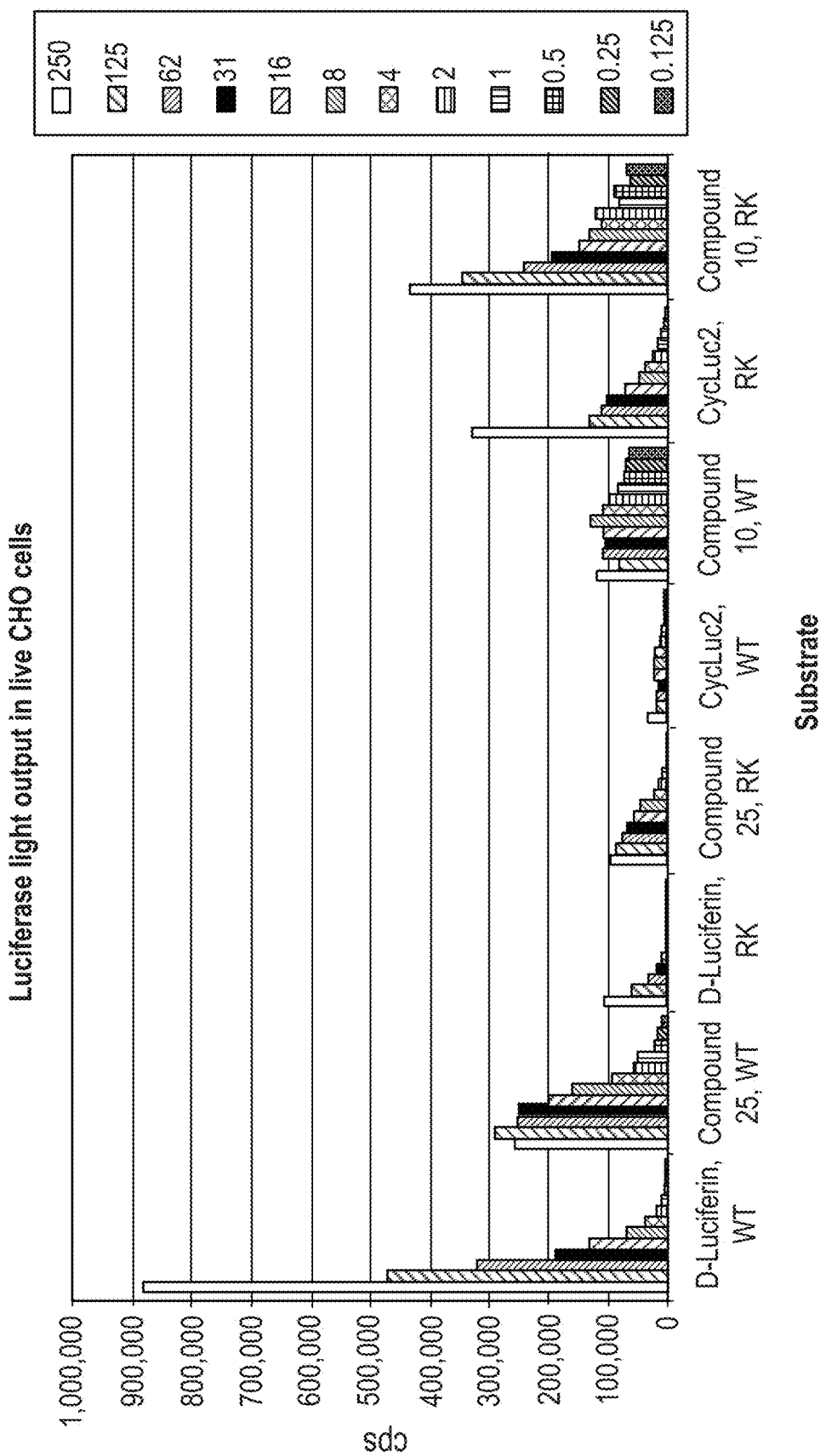
FIG. 5 is a graph illustrating that in vitro detection of FAAH activity in live CHO cells expressing a wild-type luciferase or a R218K luciferase by using two exemplary luciferin amides and their corresponding luciferins.

Compound 25 and Compound 10, as well as their corresponding luciferins (i.e., D-Luciferin and CycLuc2, respectively), were tested in live CHO cells expressing wild-type (WT) luciferase or R218K (RK) luciferase at various concentrations (i.e., 0.125 µM, 0.25 µM, 0.5 µM, 1 µM, 2 µM, 4 µM, 8 µM, 16 µM, 31 µM, 62 µM, 125 µM, and 250 µM). The results are summarized in FIG. 5. As shown in FIG. 5, cells expressing R218K luciferase and treated with Compound 10 resulted in higher light emission than all other substrate-luciferase combinations at substrate concentrations below 30 µM. At concentrations above 30 µM, light output generated in cells expressing R218K and treated with Compound 10 was only exceeded by cells expressing the wild-type luciferase and treated with D-luciferin. In addition, upon treating with Compound 10 at all concentration levels, cells expressing either the wild-type luciferase or the R218K luciferase exhibited greater light output than cells treated with Compound 10's corresponding luciferin.

EXAMPLE 24

In Vivo Assays

General Procedures
In Vivo Imaging

FVB mice were injected with AAV9-luc+ in the brain striatum. Bioluminescence assays were performed approximately nine months after AAV injection. Each luciferin amide was diluted into PBS to the indicated concentration from a 50 mM DMSO stock solution and filtered (0.22 µm) prior to intraperitoneally injection (0.1 mL per mouse). Mice were anesthetized with isoflurane (2% in 1 L/min oxygen) and images acquired on a Xenogen IVIS 100 imaging system and analyzed with Living Image software.
In Vivo FAAH Inhibition Assay Mice were injected intraperitoneally with 1 mg/mL of a specific FAAH inhibitor PF-3845 dissolved in 18:1:1 PBS:ethanol:emulphor (0.1 mL), or with an equal volume of 18:1:1 PBS:ethanol:emulphor control vehicle. Thirty minutes after injection, the mice were imaged as described above.
Results and Discussion Certain luciferin amides described herein were tested to determine whether they would image well in live mice. For these studies, FVB mice were injected with adeno-associated virus 9 (AAV9)-luciferase constructs into the brain striatum. These mice expressed luciferase exclusively in their brain tissue throughout their lifetime (many months). Because FAAH is highly expressed in brain, and inhibition of FAAH activity in the brain is necessary for the therapeutic action of FAAH inhibitors under clinical study, this model is ideal for testing the ability of luciferin amides as sensors of relevant FAAH activity in vivo.

Figure 6:
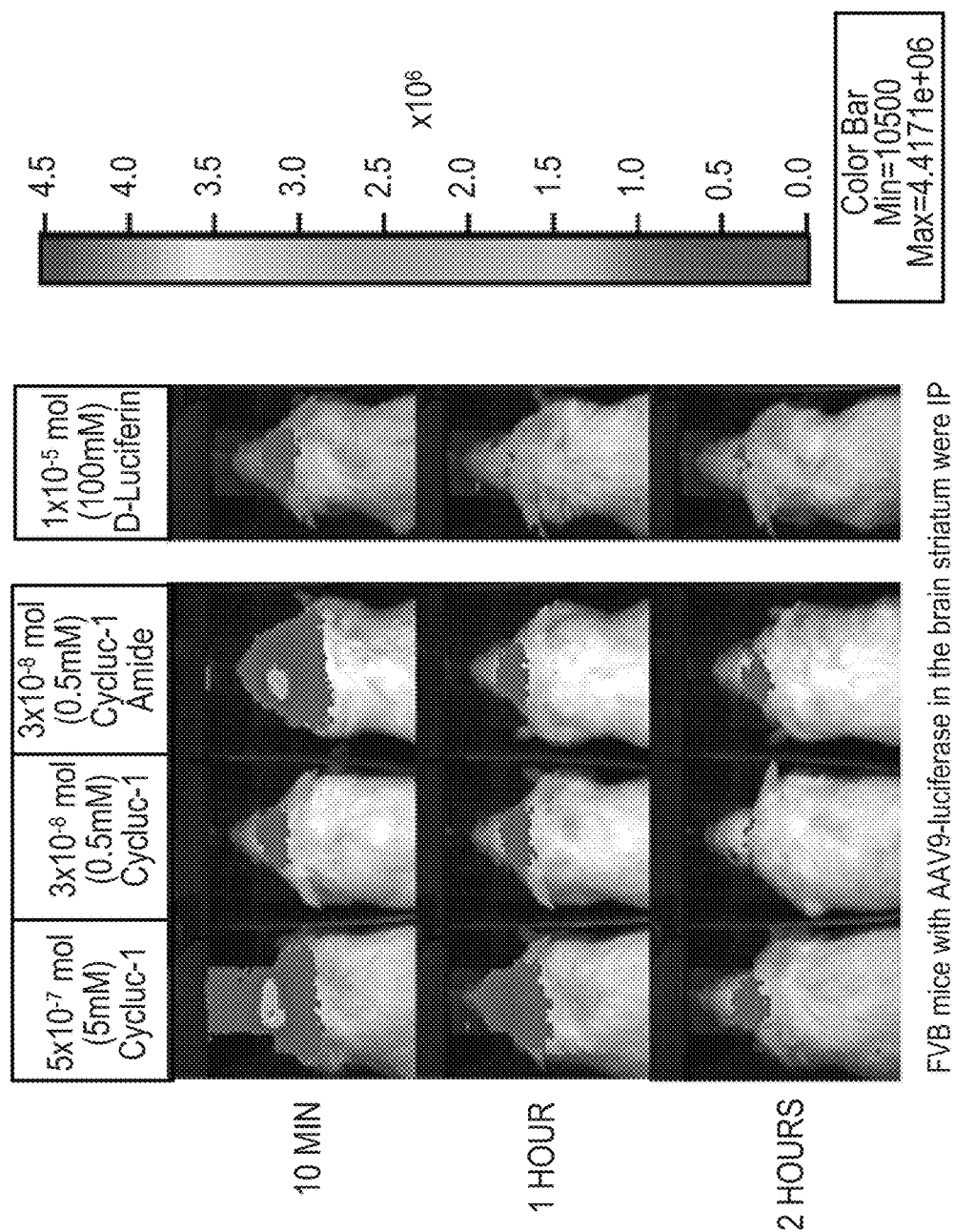
FIG. 6 is a graph comparing in vivo detection of FAAH activity in mice between a native firefly luciferin and a synthetic luciferin.

Bioluminescence imaging (BLI) in the brain is more challenging than imaging in the rest of the organism, in part because a luciferase substrate (i.e., a luciferin) must cross the blood-brain barrier. Therefore, the ability of a synthetic luciferin (i.e., Compound 9's corresponding luciferin (CycLuc1)) to allow bioluminescence imaging in these mice, as compared to the native firefly luciferase substrate (i.e., D-luciferin) was first tested. Specifically, each substrate was injected intraperitoneally (IP) in PBS at a volume of 0.1 mL, D-luciferin being at a concentration of 100 mM and CycLuc1 being at a concentration of 5 mM. The results are summarized in FIG. 6. Remarkably, as shown in FIG. 6, CycLuc1 gave an order of magnitude higher signal than D-luciferin, even when used at a 20-fold lower dose. Moreover, the signal was much more persistent, peaking at ~10 minutes, but lasting for over 2 hours. CycLuc1 was then injected at a 320-fold lower dose (0.06 mL of 0.5 mM) than D-luciferin. As shown in FIG. 6, at this dose, the signal was similar to that obtained with D-luciferin (0.1 mL of 100 mM), but again persisted for a longer time. These data show that synthetic luciferins can efficiently cross the blood-brain barrier, and their improved performance relative to D-luciferin suggests that they are better able to surmount this barrier than D-luciferin.

Having established that CycLuc1 can advantageously be utilized for BLI in the brains of live mice, a test was conducted to determine whether the amide form of CycLuc1 (i.e., Compound 9)—not itself a substrate for firefly luciferase—could be delivered into the brain, where it could be subsequently metabolized into CycLuc1 by endogenous FAAH activity. Specifically, Compound 9 (i.e., CycLuc1 amide) was injected at 0.5 mM in 0.5% DMSO/PBS (0.06 mL). FIG. 6 shows that, despite the 320-fold lower injected dose compared to D-luciferin, its bioluminescent light output was again over an order of magnitude greater than that obtained from the standard imaging conditions with D-luciferin. In addition, the light emission from Compound 9 exceeded that obtained from an equivalent dose of CycLuc1 itself, and nearly equaling to the light emission obtained from the 5 mM CycLuc1 dose. These results show that the luciferin amide Compound 9 exhibited improved ability to enter the brains of live mice, and was rapidly converted to a luciferin substrate in brain tissue. Thus, Compound 9 could offer further improved performance over D-luciferin and even the parent CycLuc1, at lower injected doses.

Figure 7:
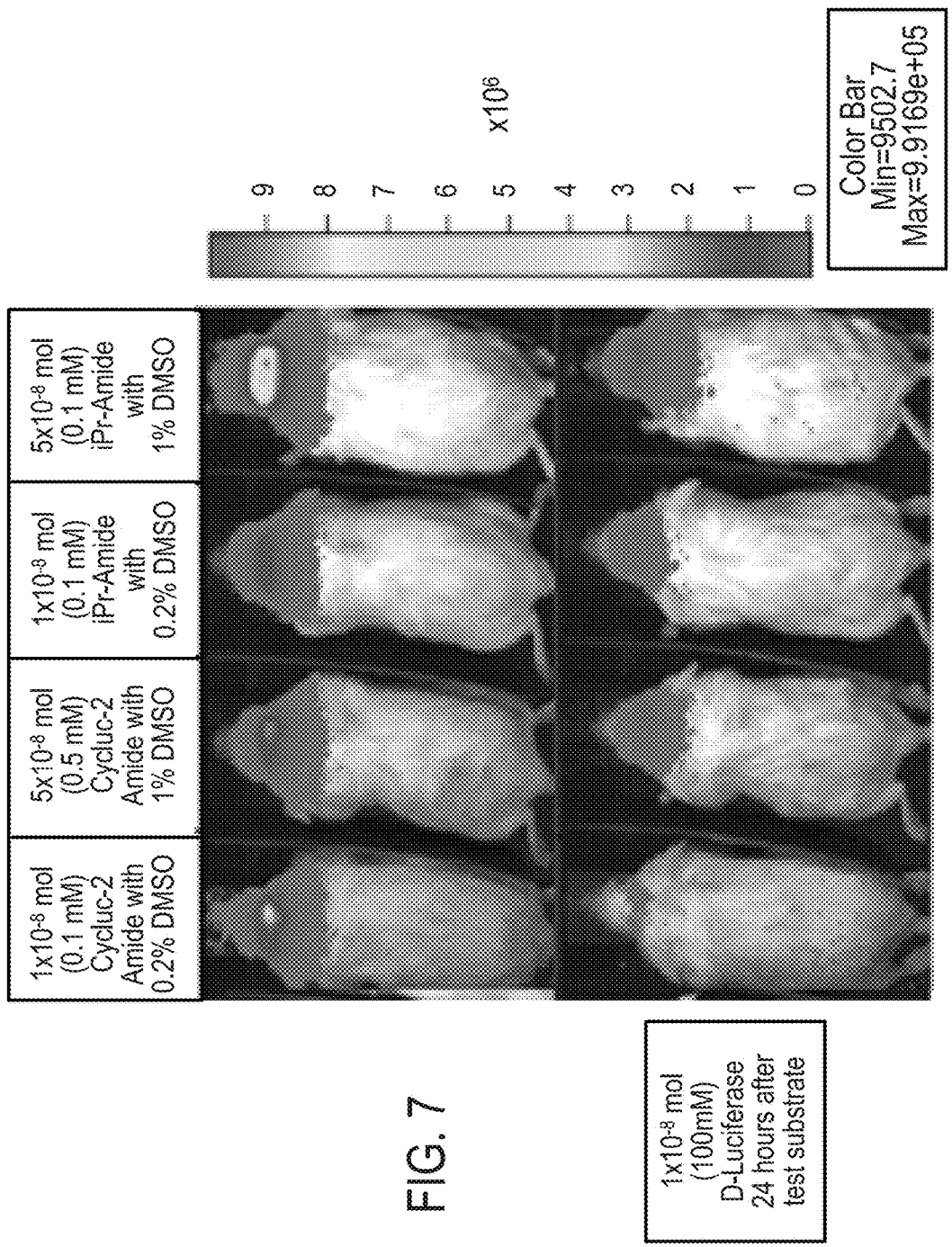
FIG. 7 is a graph comparing in vivo detection of FAAH activity in mice between a native firefly luciferin and two exemplary luciferin amides.

To determine if the above findings were general, two additional amides, i.e., Compound 5 (iPrNH-luciferin amide) and Compound 10 (CycLuc2 amide), were tested in mice at doses 200-fold and 1000-fold lower than the standard doses used for imaging with D-luciferin. The imaging results are shown in FIG. 7. In this figure, mice in the top row were treated with luciferin amides in the amounts indicated in the figure, and the mice in the bottom row were the same mice that were imaged one day later using a standard dose of D-luciferin. As shown in FIG. 7, despite the much lower doses, bioluminescence signals obtained from Compounds 5 and 10 were respectively 5-fold to 10-fold higher than that obtained from the standard D-luciferin imaging conditions.

The above general findings were also extended to a number of other related luciferin amides, including Compound 1 (MeNH luciferin amide), Compound 3 (iBuNH-luciferin amide), Compound 4 (PropanolNH-luciferin amide), Compound 6 (EtNH luciferin amide), Compound 7 (EtNH-luciferin methylamide), and Compound 25 (D-luciferin amide). The results show that Compounds 1, 3, 6, and 7 gave relatively strong light emission, while Compounds 4 and 25 and Me2N-luciferin methyl ester (a corresponding ester of Compound 2) gave relatively weak light emission. Without wishing to be bound by theory, the above results suggest that hydrophobicity of a substrate could be important for allowing the substrate to enter cells and cross the blood-brain barrier. In addition, secondary amides (e.g., methyl amide, ethanolamine, and the like) gave similar light emission to primary amides, but esters gave relatively weak limit emission, potentially because they can be cleaved elsewhere, have poorer pharmacokinetic properties, and/or are poorer substrates for FAAH.

Certain luciferin amides exhibited stronger light emission at much lower doses than its corresponding luciferin. For example, photon flux obtained from Compound 14's corresponding luciferin (5 mM) exceeded that obtained from 100 mM of D-luciferin by more than 5-fold, but Compound 14 gave more than 10-fold improved signal even at 0.1 mM. See Table 1. These results demonstrates that the luciferin amides described herein can be efficiently converted into luciferase substrates (i.e., luciferins), and that these molecules allow improved bioluminescence imaging in the brains of live mice with much lower injection doses (e.g., more than 1000-fold lower). Luciferin amides are therefore of great utility for enhanced in vivo BLI studies, and for standard studies where lower substrate dosage is desired for cost savings. In some embodiments, a luciferin amide can be used at a lower dose, while exhibiting performance equivalent to or better than D-luciferin. For example, as shown in Table 1 below, even at a 5000-fold lower IP dose (i.e., 20 µM), Compound 5 yielded higher photon flux than the standard 100 mM D-luciferin. At a 25,000-fold lower dose (i.e., 4 µM), Compound 5 gave ~30% of the D-luciferin signal.

TABLE 1

| Photon flux (p/s) after treatment with luciferin analogs. | |
|---|---|
| Compound 14's corresponding luciferin (5 mM) | 6.69E+06 |
| Compound 14 (100 µM) | 1.43E+07 |
| D-luciferin (100 mM) | 1.21E+06 |
| Compound 5 (4 µM) | 2.97E+05 |
| Compound 5 (20 µM) | 1.95E+06 |
| Compound 5 (100 µM) | 7.84E+06 |
| Compound 5 (500 µM) | 1.19E+07 |

Figure 8:
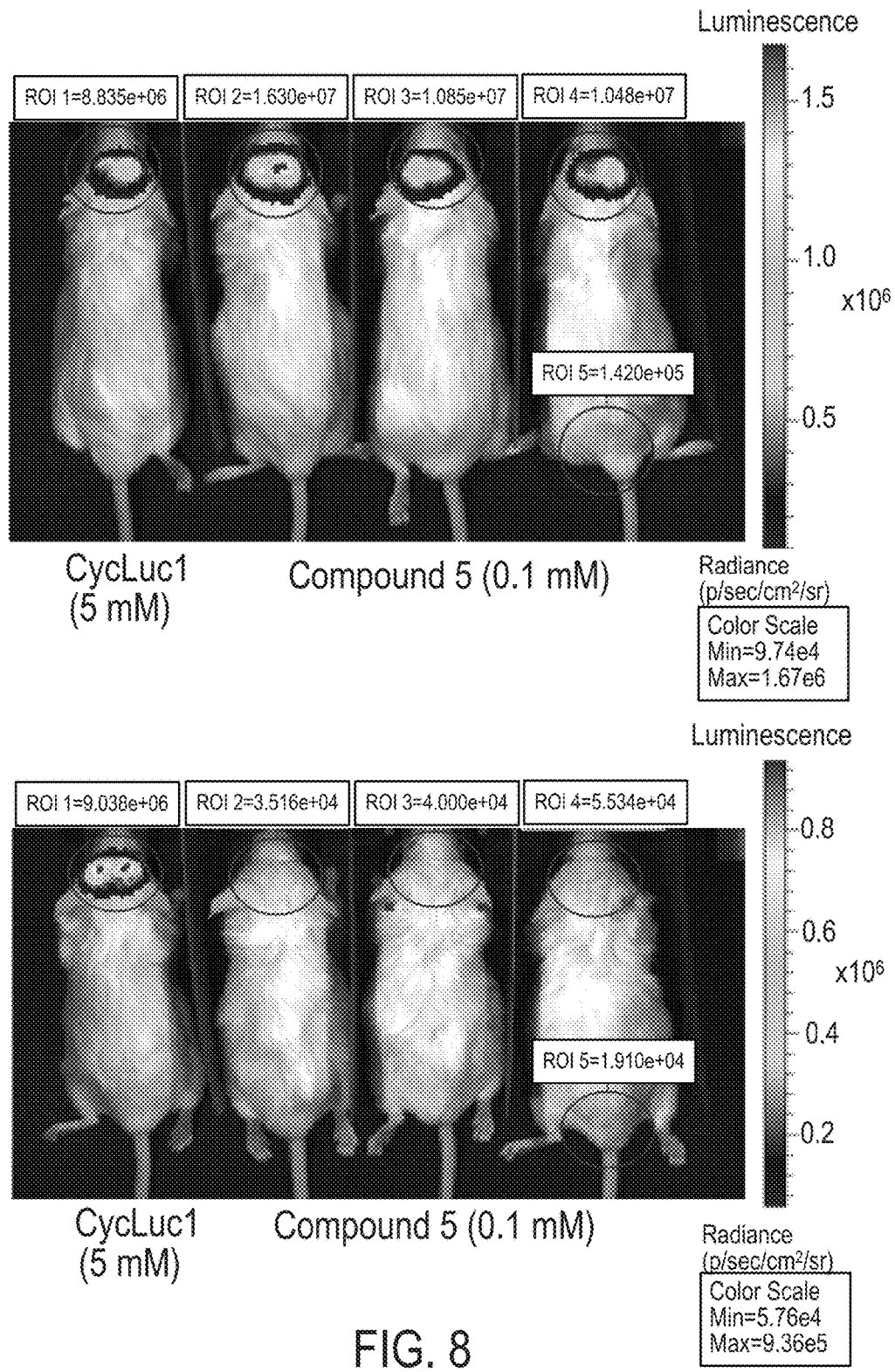
FIG. 8 is a graph comparing in vivo detection of FAAH activity in mice between a luciferin and a luciferin amide in the presence or absence of a FAAH inhibitor.

FAAH is highly expressed in most tissues, particularly in the brain. To determine whether the luciferin amides are cleaved exclusively by FAAH in the brain tissue, eight FVB mice expressing AAV9-luciferase in the striatum were divided into two groups: (1) four mice were injected IP with 1 mg/mL of a specific FAAH inhibitor PF-3845 dissolved in 18:1:1 PBS:ethanol:emulphor (0.1 mL), and (2) four mice were treated with an equal volume of 18:1:1 PBS:ethanol:emulphor control vehicle without PF-3845. After 30 minutes, one mouse from each group was IP injected with 5 mM CycLuc1 (i.e., Compound 9's corresponding luciferin) in PBS (0.1 mL), and three were injected with 0.1 mM Compound 5 in 0.2% DMSO/PBS (0.1 mL). The mice were imaged 10 minutes after substrate injection. The results are summarized in FIG. 8. Mice in the right panel were group (1) (i.e., treated with a FAAH inhibitor) and mice in the left panel were from group (2) (i.e., without being treated with a FAAH inhibitor). As shown in FIG. 8, the light output from mice injected with CycLuc1 was unchanged in groups (1) and (2) (total photon flux of $9\times10^6$ p/s), while the total photon flux from mice treated with Compound 5 was reduced by nearly three orders of magnitude in group (1), from an average of $1.3\times10^7$ p/s down to $4.4\times10^4$ p/s. The results demonstrate that luciferin amides are selectively cleaved by FAAH in the brains of live mice.

The above tests suggest that luciferin amides can be used for non-invasive imaging of FAAH activity in live mice. Currently, inhibition of FAAH activity in the mouse brain after treatment with FAAH inhibitors is assessed postmortem, by performing radioactive HPLC assays on the brain tissue. Thus, use of the luciferin amides described herein as bioluminescent sensors of FAAH activity that could measure this inhibition longitudinally in a live mouse would be an enabling technology with numerous industrial applications.

Other embodiments are within the scope of the following claims.

What is claimed is:
1. A compound of formula (I):

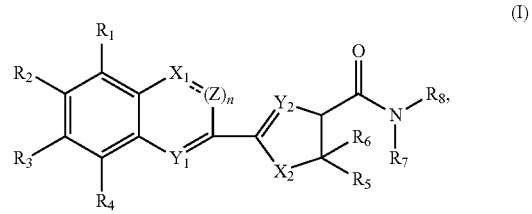

wherein
n is 0 or 1;
═ is deleted, a single bond, or a double bond; provided that, when n is 0, ═ is deleted;
each of $X_1$ and $X_2$, independently, is O, S, Se, N, N($R_a$), C($R_a$), or C($R_aR_a'$), in which each of $R_a$ and $R_a'$, independently, is H or $C_1$-$C_{10}$ alkyl; provided that, when ═ is a double bond, $X_1$ is N or C($R_a$);
each of $Y_1$ and $Y_2$, independently, is N or C($R_b$), in which $R_b$ is H or $C_1$-$C_{10}$ alkyl;
Z is C($R_c$) or C($R_cR_c'$), in which each of $R_c$ and $R_c'$, independently, is H or $C_1$-$C_{10}$ alkyl; provided that, when ═ is a single bond, Z is C($R_cR_c'$) and that, when ═ is a double bond, Z is C($R_c$);
$R_2$ is N($R_dR_d'$), in which $R_d$ is H, $C_1$-$C_{10}$ alkyl optionally substituted with OH, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; $R_{d'}$ is $C_1$-$C_{10}$ alkyl optionally substituted with OH, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; or $R_2$ and $R_1$, together with the carbon atoms to which they are attached, are a substituted or unsubstituted piperidinyl ring; or when $R_2$ and $R_1$, together with the carbon atoms to which they are attached, are a substituted or unsubstituted piperidinyl ring, $R_2$ and $R_3$, together with the carbon atoms to which they are attached, are a substituted or unsubstituted 5, 6, or 7-membered ring optionally fused with one or more substituted or unsubstituted 5, 6, or 7-membered rings;
each of $R_1$, $R_3$, $R_4$, $R_5$, and $R_6$, independently, is H, halo, CN, O$R_e$, S$R_e$, NO$_2$, N($R_eR_e'$), $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, in which each of $R_e$ and $R_e'$, independently, is H or $C_1$-$C_{10}$ alkyl; or $R_1$ and $R_2$, together with the carbon atoms to which they are attached, are a substituted or unsubstituted piperidinyl ring; or when $R_1$ and $R_2$, together with the carbon atoms to which they are attached, are a substituted or unsubstituted piperidinyl ring, $R_2$ and $R_3$, together with the carbon atoms to which they are attached, are a substituted or unsubstituted 5, 6, or 7-membered ring optionally fused with one or more substituted or unsubstituted 5, 6, or 7-membered rings; and each of $R_7$ and $R_8$, independently, is H or $C_1$-$C_3$ alkyl optionally substituted with OH.

2. The compound of claim 1, wherein n is 0 and ═ is deleted.

3. The compound of claim 2, wherein each of $X_1$ and $X_2$ is S and each $Y_1$ and $Y_2$ is N.

4. The compound of claim 3, wherein $R_2$ is $N(R_dR_d')$, in which each of $R_d$ is H or $C_1$-$C_{10}$ alkyl optionally substituted with OH, and $R_d'$ is $C_1$-$C_{10}$ alkyl optionally substituted with OH.

5. The compound of claim 4, wherein each of $R_d$ is H, $CH_3$, $CH_2CH_3$, $CH(CH_3)_2$, $(CH_2)_3$-OH, or $CH_2CH(CH_3)_2$, and $R_d'$ is $CH_3$, $CH_2CH_3$, $CH(CH_3)_2$, $(CH_2)_3$-OH, or $CH_2CH(CH_3)_2$.

6. The compound of claim 5, wherein each of $R_1$, $R_3$, $R_4$, $R_5$, and $R_6$ is H.

7. The compound of claim 6, wherein each of $R_7$ and $R_8$, independently, is H or $C_1$-$C_2$ alkyl optionally substituted with OH.

8. The compound of claim 7, wherein each of $R_7$ and $R_8$, independently, is H, $CH_3$, or $CH_2CH_2OH$.

9. The compound of claim 6, wherein the compound is

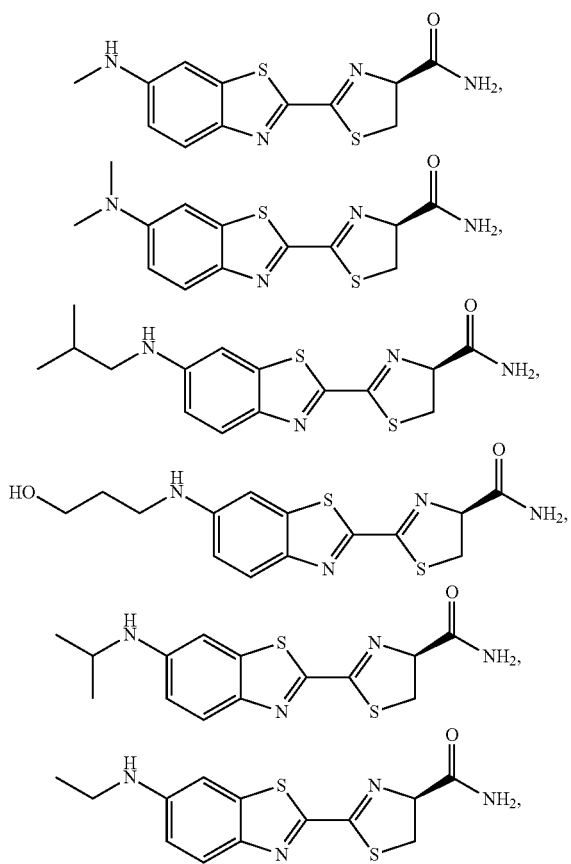

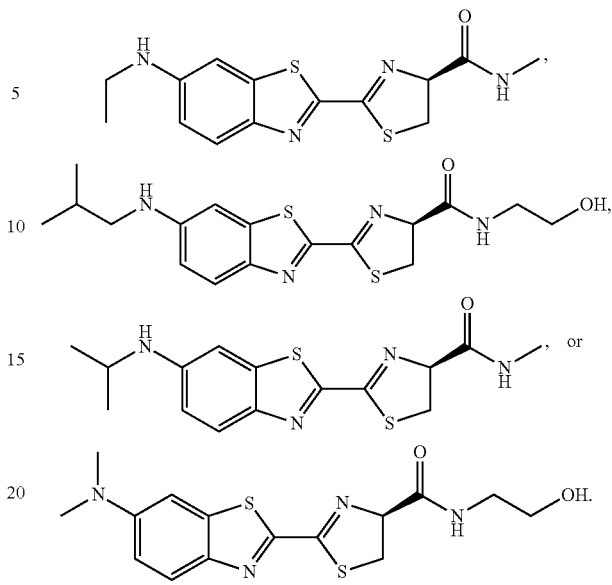

10. A compound of formula (I):

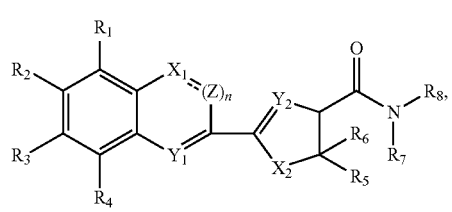

(I)

wherein n is 0;

═ is deleted;

each of $X_1$ and $X_2$ is S;

each of $Y_1$ and $Y_2$ is N;

Z is $C(R_c)$ or $C(R_cR_c')$, in which each of $R_c$ and $R_c'$, independently, is H or $C_1$-$C_{20}$ alkyl; provided that, when ═ is a single bond, Z is $C(R_cR_c')$ and that, when ═ is a double bond, Z is $C(R_c)$;

$R_2$ and $R_1$ together with the carbon atoms to which they are attached, are a piperidinyl ring optionally substituted with $C_1$-$C_{10}$ alkyl;

each of $R_3$, $R_4$, $R_5$, and $R_6$, independently, is H, halo, CN, $OR_e$, $SR_e$, $NO_2$, $N(R_eR_e')$, $C_1$-$C_{10}$ alkyl, $C_2$-$C_{10}$ alkenyl, $C_2$-$C_{10}$ alkenyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, in which each of $R_e$ and $R_e'$, independently, is H or $C_1$-$C_{10}$ alkyl; and each of $R_7$ and $R_8$, independently, is H or $C_1$-$C_3$ alkyl optionally substituted with OH.

11. The compound of claim 10, wherein $R_1$ and $R_2$, together with the carbon atoms to which they are attached, are a piperidinyl ring optionally substituted with $CH_3$.

12. The compound of claim 11, wherein each of $R_3$, $R_4$, $R_8$, $R_6$, $R_7$, and $R_8$ is H.

13. The compound of claim 12, wherein the compound is

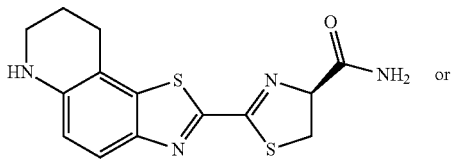

or

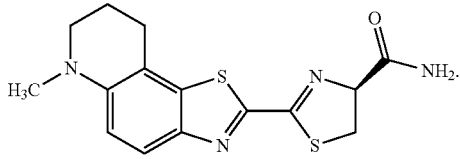

14. A compound of formula (I):

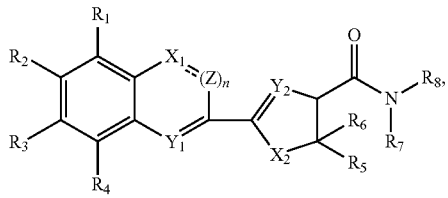

wherein n is 0;

═ is deleted;

each of $X_1$ and $X_2$ is S;

each of $Y_1$ and $Y_2$ is N;

Z is $C(R_c)$ or $C(R_cR_c')$, in which each of $R_c$ and $R_c'$, independently, is H or $C_1$-$C_{10}$ alkyl; provided that, when ═ is a single bond, Z is $C(R_cR_c')$ and that, when ═ is a double bond, Z is $C(R_c)$;

$R_2$ and R, together with the carbon atoms to which they are attached, are a piperidinyl ring optionally substituted with $C_1$-$C_{10}$ alkyl, and $R_2$ and $R_3$, together with the carbon atoms to which they are attached, are a 6-membered ring optionally substituted with $C_1$-$C_{10}$ alkyl;

each of $R_4$, $R_5$, and $R_6$, independently, is H, halo, CN, $OR_e$, $SR_e$, $NO_2$, $N(R_eR_e)$, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, in which each of $R_e$ and $R_e'$, independently, is H or $C_1$-$C_{10}$ alkyl; and each of $R_7$ and $R_8$, independently, is H or $C_1$-$C_3$ alkyl optionally substituted with OH.

15. The compound of claim 14, wherein $R_1$ and $R_2$, together with the carbon atoms to which they are attached, are a piperidinyl ring and $R_2$ and $R_3$, together with the carbon atoms to which they are attached, are a 6-membered ring.

16. The compound of claim 15, wherein each of $R_4$, $R_5$, $R_6$, $R_7$, and $R_8$ is H.

17. The compound of claim 16, wherein the compound is

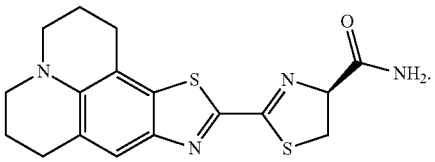 [SMILES: NC(=O)[C@H]1CSC(c2nc3cc4c5c(c3s2)CCCN5CCC4)=N1]

18. The compound of claim 1, wherein the compound is a D-isomer.

19. An imaging method, comprising:
contacting a cell comprising a luciferase and a fatty acid amide hydrolase with the compound of formula (I):

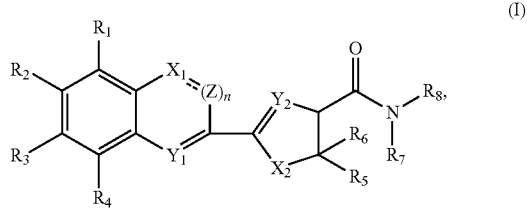

wherein n is 0 or 1;

═ is deleted, a single bond, or a double bond; provided that, when n is 0, ═ is deleted;

each of $X_1$ and $X_2$, independently, is O, S, Se, N, $N(R_a)$, $C(R_a)$, or $C(R_aR_a')$, in which each of $R_a$ and $R_a'$ independently, is H or $C_1$-$C_{10}$ alkyl; provided that, when ═ is a double bond, $X_1$ is N or $C(R_a)$;

each of $Y_1$ and $Y_2$, independently, is N or $C(R_b)$, in which Rb is H or $C_1$-$C_{10}$ alkyl;

Z is $C(R_c)$ or $C(R_cR_c')$, in which each of $R_c$ and $R_c'$, independently, is H or $C_1$-$C_{10}$ alkyl; provided that, when ═ is a single bond, Z is $C(R_cR_c')$ and that, when ═ is a double bond, Z is $C(R_c)$;

$R_2$ is $N(R_aR_d)$, in which each of $R_d$ and $R_d'$, independently, is H, $C_1$-$C_{10}$ alkyl optionally substituted with OH, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, or heteroaryl; or $R_2$ and $R_1$ together with the carbon atoms to which they are attached, are a substituted or unsubstituted piperidinyl ring; or when $R_2$ and $R_1$, together with the carbon atoms to which they are attached, are a substituted or unsubstituted piperidinyl ring, $R_2$ and $R_3$, together with the carbon atoms to which they are attached, are a substituted or unsubstituted 5, 6, or 7-membered ring optionally fused with one or more substituted or unsubstituted 5, 6, or 7-membered rings;

each of $R_1$, $R_3$, $R_4$, $R_5$, and $R_6$, independently, is H, halo, CN, $OR_e$, $SR_e$, $NO_2$, $N(R_eR_e')$, $C_1$-$C_{10}$ alkyl, $C_2$-$C_{10}$ alkenyl, $C_2$-$C_{10}$ alkynyl, $C_3$-$C_{20}$ cycloalkyl, $C_3$-$C_{20}$ cycloalkenyl, $C_1$-$C_{20}$ heterocycloalkyl, $C_1$-$C_{20}$ heterocycloalkenyl, aryl, heteroaryl, in which each of $R_e$ and $R_e'$, independently, is H or $C_1$-$C_{10}$ alkyl; or $R_1$ and $R_2$, together with the carbon atoms to which they are attached, are a substituted or unsubstituted piperidinyl ring; or when $R_1$ and $R_2$, together with the carbon atoms to which they are attached, are a substituted or unsubstituted piperidinyl ring, $R_2$ and $R_3$, together with the carbon atoms to which they are attached, are a substituted or unsubstituted 5, 6, or 7-membered ring optionally fused with one or more substituted or unsubstituted 5, 6, or 7-membered rings; and each of $R_7$ and $R_8$, independently, is H or $C_1$-$C_3$ alkyl optionally substituted with OH; and detecting bioluminescent emission from the cell.

20. The method of claim 19, wherein the luciferase is a wild-type luciferase.

21. The method of claim 20, wherein the wild-type luciferase is a beetle luciferase.

22. The method of claim 21, wherein the beetle luciferase is a firefly, click beetle, or railroad worm luciferase.

23. The method of claim 19, wherein the luciferase is a mutated luciferase.

24. The method of claim 19, wherein the contacting step is performed in a brain of a subject.

25. An imaging method, comprising:
contacting a cell comprising a fatty acid amide hydrolase with the compound of claim 1;
introducing a luciferase; and
detecting bioluminescent emission.

* * * * *

UNITED STATES PATENT AND TRADEMARK OFFICE
CERTIFICATE OF CORRECTION

| | | |
|---|---|---|
| PATENT NO. | : 9,814,787 B2 | |
| APPLICATION NO. | : 15/172509 | |
| DATED | : November 14, 2017 | |
| INVENTOR(S) | : Stephen C. Miller | |

It is certified that error appears in the above-identified patent and that said Letters Patent is hereby corrected as shown below:

In Claim 1
Column 32, Line 37, delete "$X_1$and" and insert --$X_1$ and--.
Column 32, Line 47, delete "$C_1$ –$C_{10}$" and insert --$C_1$-$C_{10}$--.
Column 33, Line 2, delete "$R_1$and" and insert --$R_1$ and--.

In Claim 11
Column 34, Line 62, delete "$R_1$and" and insert --$R_1$ and--.

In Claim 12
Column 34, Line 66, delete "$R_8$, $R_6$," and insert --$R_5$, $R_6$,--.

In Claim 14
Column 35, Line 45, delete "R," and insert --$R_1$,--.
Column 35, Line 51, delete "$R_6$ ," and insert --$R_6$,--.
Column 35, Line 52, delete "$SR_e$ , $NO_2$ , $N(R_eR_e)$," and insert --$SR_e$, $NO_2$, $N(ReRe\cdot)$,--.

In Claim 15
Column 35, Line 61, delete "$R_1$and" and insert --$R_1$ and--.

In Claim 19
Column 36, Line 33, delete "$R_a$." and insert --$R_{a'}$,--.
Column 36, Line 36, delete "Rb" and insert --$R_b$--.
Column 36, Line 41, delete "$N(R_aR_d)$," and insert --$N(R_dR_{d'})$,--.

Signed and Sealed this
Twenty-fourth Day of April, 2018

Andrei Iancu
*Director of the United States Patent and Trademark Office*